US008034346B2

(12) United States Patent
Shelton et al.

(10) Patent No.: US 8,034,346 B2
(45) Date of Patent: *Oct. 11, 2011

(54) METHODS FOR TREATING PAIN BY ADMINISTERING A NERVE GROWTH FACTOR ANTAGONIST AND AN NSAID AND COMPOSITIONS CONTAINING THE SAME

(75) Inventors: David L. Shelton, Oakland, CA (US); German J. Vergara, Moraga, CA (US); Carole M. Loo, San Mateo, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/644,087

(22) Filed: Dec. 22, 2009

(65) Prior Publication Data

US 2010/0143355 A1    Jun. 10, 2010

Related U.S. Application Data

(63) Continuation of application No. 10/783,730, filed on Feb. 19, 2004, now Pat. No. 7,655,231.

(60) Provisional application No. 60/448,823, filed on Feb. 19, 2003, provisional application No. 60/448,853, filed on Feb. 19, 2003.

(51) Int. Cl.
*A61K 39/395* (2006.01)
*C07K 16/22* (2006.01)
*C12P 21/06* (2006.01)

(52) U.S. Cl. ............... 424/145.1; 424/130.1; 424/133.1; 530/387.1; 530/387.3; 530/388.24

(58) Field of Classification Search .................. None
See application file for complete search history.

(56) References Cited

U.S. PATENT DOCUMENTS

| | | | |
|---|---|---|---|
| 3,773,919 A | 11/1973 | Boswell et al. |
| 4,389,404 A | 6/1983 | Zhorov et al. |
| 4,485,045 A | 11/1984 | Regen |
| 4,544,545 A | 10/1985 | Ryan et al. |
| 4,676,980 A | 6/1987 | Segal et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 5,013,556 A | 5/1991 | Woodle et al. |
| 5,047,335 A | 9/1991 | Paulson et al. |
| 5,130,311 A | 7/1992 | Guillaumet et al. |
| 5,147,294 A | 9/1992 | Smith et al. |
| 5,219,740 A | 6/1993 | Miller et al. |
| 5,278,299 A | 1/1994 | Wong et al. |
| 5,342,942 A | 8/1994 | Jaen et al. |
| 5,409,944 A | 4/1995 | Black et al. |
| 5,422,120 A | 6/1995 | Kim |
| 5,436,265 A | 7/1995 | Black et al. |
| 5,475,995 A | 12/1995 | Livingston |
| 5,500,362 A | 3/1996 | Robinson et al. |
| 5,510,261 A | 4/1996 | Goochee et al. |
| 5,510,368 A | 4/1996 | Lau et al. |
| 5,521,213 A | 5/1996 | Prasit et al. |
| 5,530,101 A | 6/1996 | Queen et al. |
| 5,536,752 A | 7/1996 | Ducharme et al. |
| 5,545,806 A | 8/1996 | Lonberg et al. |
| 5,545,807 A | 8/1996 | Surani et al. |
| 5,550,142 A | 8/1996 | Ducharme et al. |
| 5,552,422 A | 9/1996 | Gauthier et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,625,126 A | 4/1997 | Lonberg et al. |
| 5,633,425 A | 5/1997 | Lonberg et al. |
| 5,639,780 A | 6/1997 | Lau et al. |
| 5,656,435 A | 8/1997 | Nakahama et al. |
| 5,661,016 A | 8/1997 | Lonberg et al. |
| 5,693,761 A | 12/1997 | Queen et al. |
| 5,693,762 A | 12/1997 | Queen et al. |

(Continued)

FOREIGN PATENT DOCUMENTS

EP          0345242       12/1989

(Continued)

OTHER PUBLICATIONS

Rudikoff et al. (1982). Single amino acid substitution altering antigen-binding specificity. Proc. Natl. Acad. Sci. USA. 79:1979-1983.*
ATCC Search Results for "911 Mab" located at http://www.atcc.org/common/catalog/wordSearch/results.cfm., last visited Aug. 30, 2006, one page.
Abbadie, C., et al., "Impaired Neuropathic Pain Responses in Mice Lacking the Chemokine Receptor CCR2", Proc. Natl. Acad. Sci., Jun. 24, 2003, pp. 7947-7952, 100(13).
Aloe, L., et al., "The Synovium of Transgenic Arthritic Mice Expressing Human Tumor Necrosis Factor Contains a High Level of Nerve Growth Factor", Growth Factors, 1993, pp. 149-155, 9(2).
Aloe, L., et al., "Nerve Growth Factor in the Synovia of Patients with Rheumatoid Arthritis: Correlation with TNF-α and IL-1β and Possible Functional Significance", Clin. Exp. Rheumatol., Sep.-Oct. 1999, pp. 632-633, 17(5).
Altschul, S.F., et al., "Gapped BLAST and PSI-BLAST: A New Generation of Protein Database Search Programs", Nucleic Acids Res., 1997, pp. 3389-3402, 25(17).

(Continued)

*Primary Examiner* — Christine J Saoud
*Assistant Examiner* — Jon M Lockard
(74) *Attorney, Agent, or Firm* — Pfizer Inc.

(57) ABSTRACT

The present invention features methods for treating or preventing pain comprising administering an amount of a nerve growth factor antagonist (such as an anti-NGF antibody) and an amount of an NSAID such that together they provide effective pain relief. The invention also features compositions comprising a nerve growth factor antagonist and an NSAID and kits containing the same.

12 Claims, 2 Drawing Sheets

U.S. PATENT DOCUMENTS

Figure 1:
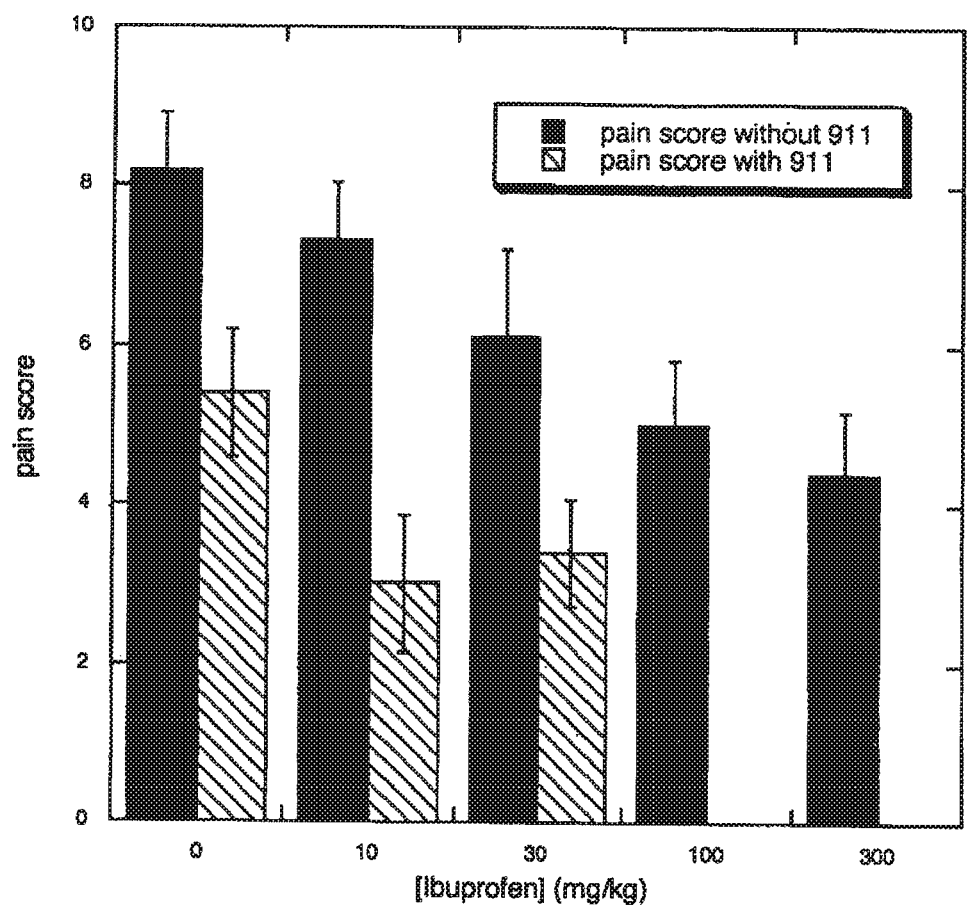

| | | | |
|---|---|---|---|
| 5,712,100 A | 1/1998 | Nakahama et al. |
| 5,733,743 A | 3/1998 | Johnson et al. |
| 5,750,373 A | 5/1998 | Garrard et al. |
| 5,766,863 A | 6/1998 | Godowski et al. |
| 5,807,715 A | 9/1998 | Morrison et al. |
| 5,814,482 A | 9/1998 | Dubensky, Jr. et al. |
| 5,821,337 A | 10/1998 | Carter et al. |
| 5,843,942 A | 12/1998 | Breault et al. |
| 5,844,092 A | 12/1998 | Presta et al. |
| 5,866,692 A | 2/1999 | Shitara et al. |
| 5,877,016 A | 3/1999 | Presta et al. |
| 5,891,650 A | 4/1999 | Godowski et al. |
| 5,981,568 A | 11/1999 | Kunz et al. |
| 5,997,867 A | 12/1999 | Waldmann et al. |
| 6,017,878 A | 1/2000 | Saragovi et al. |
| 6,022,875 A | 2/2000 | Zimmer et al. |
| 6,027,927 A | 2/2000 | Presta et al. |
| 6,054,297 A | 4/2000 | Carter et al. |
| 6,127,401 A | 10/2000 | Singh et al. |
| 6,153,189 A | 11/2000 | Presta et al. |
| 6,180,370 B1 | 1/2001 | Queen et al. |
| 6,180,377 B1 | 1/2001 | Morgan et al. |
| 6,210,671 B1 | 4/2001 | Co |
| 6,265,150 B1 | 7/2001 | Terstappen et al. |
| 6,291,247 B1 | 9/2001 | Riopelle et al. |
| 6,306,849 B1 | 10/2001 | Hudkins et al. |
| 6,331,415 B1 | 12/2001 | Cabilly et al. |
| 6,350,861 B1 | 2/2002 | Co et al. |
| 6,359,130 B1 | 3/2002 | Singh et al. |
| 6,376,471 B1 | 4/2002 | Lawrence, III et al. |
| 6,399,780 B1 | 6/2002 | Hudkins |
| 6,413,942 B1 | 7/2002 | Felgner et al. |
| 6,436,908 B1 | 8/2002 | Koch et al. |
| 6,492,380 B1 | 12/2002 | Ross et al. |
| 6,506,559 B1 | 1/2003 | Driver et al. |
| RE38,103 E | 4/2003 | Guay et al. |
| 6,548,062 B2 | 4/2003 | Buchkovich et al. |
| 6,548,640 B1 | 4/2003 | Winter |
| 6,649,605 B2 | 11/2003 | Olesen et al. |
| 6,919,426 B2 | 7/2005 | Boone et al. |
| 7,252,822 B2 | 8/2007 | Shelton et al. |
| 7,255,860 B2 | 8/2007 | Shelton et al. |
| 7,449,616 B2 | 11/2008 | Pons et al. |
| 2001/0046959 A1 | 11/2001 | Buchkovich et al. |
| 2002/0028779 A1 | 3/2002 | High et al. |
| 2002/0072543 A1 | 6/2002 | Olesen et al. |
| 2002/0146416 A1 | 10/2002 | Presta et al. |
| 2003/0008807 A1 | 1/2003 | Levine et al. |
| 2003/0072746 A1 | 4/2003 | Miller |
| 2003/0203923 A1 | 10/2003 | Ross et al. |
| 2004/0038874 A1 | 2/2004 | Omoigui |
| 2004/0071701 A1 | 4/2004 | Delafoy et al. |
| 2004/0097562 A1 | 5/2004 | Olesen et al. |
| 2004/0121959 A1 | 6/2004 | Boone et al. |
| 2004/0131615 A1 | 7/2004 | Shelton et al. |
| 2004/0228862 A1 | 11/2004 | Shelton et al. |
| 2004/0237124 A1 | 11/2004 | Pons et al. |
| 2005/0074821 A1 | 4/2005 | Wild, Jr. et al. |
| 2005/0222035 A1 | 10/2005 | Boone et al. |
| 2005/0265994 A1 | 12/2005 | Shelton et al. |

FOREIGN PATENT DOCUMENTS

| | | |
|---|---|---|
| EP | 0418590 | 3/1991 |
| EP | 0519596 | 12/1992 |
| EP | 0524968 | 2/1993 |
| FR | 2807660 | 10/2001 |
| GB | 2200651 | 8/1988 |
| JP | 63295588 | 12/1988 |
| JP | 03163095 | 7/1991 |
| JP | 05076384 | 3/1993 |
| JP | 06317587 | 11/1994 |
| WO | WO8704462 | 7/1987 |
| WO | WO8909225 | 10/1989 |
| WO | WO9007936 | 7/1990 |
| WO | WO9010644 | 9/1990 |
| WO | WO9011092 | 10/1990 |
| WO | WO9100360 | 1/1991 |
| WO | WO9102805 | 3/1991 |
| WO | WO9114445 | 10/1991 |
| WO | WO9220373 | 11/1992 |
| WO | WO9303769 | 3/1993 |
| WO | WO9325234 | 3/1993 |
| WO | WO9306213 | 4/1993 |
| WO | WO9325698 | 4/1993 |
| WO | WO9310218 | 5/1993 |
| WO | WO9311230 | 6/1993 |
| WO | WO9319191 | 9/1993 |
| WO | WO9403622 | 2/1994 |
| WO | WO9404690 | 3/1994 |
| WO | WO9412649 | 6/1994 |
| WO | WO9423697 | 10/1994 |
| WO | WO9428938 | 12/1994 |
| WO | WO9500655 | 1/1995 |
| WO | WO9507994 | 3/1995 |
| WO | WO9511984 | 5/1995 |
| WO | WO9513796 | 5/1995 |
| WO | WO9525795 | 9/1995 |
| WO | WO9530763 | 11/1995 |
| WO | WO9617072 | 6/1996 |
| WO | WO9715593 | 5/1997 |
| WO | WO9721732 | 6/1997 |
| WO | WO9742338 | 11/1997 |
| WO | WO9806048 | 2/1998 |
| WO | WO9817278 | 4/1998 |
| WO | WO9819674 | 5/1998 |
| WO | WO9953055 | 10/1999 |
| WO | WO9958572 | 11/1999 |
| WO | WO0053211 | 9/2000 |
| WO | WO0069829 | 11/2000 |
| WO | WO0073344 | 12/2000 |
| WO | WO0127160 | 4/2001 |
| WO | WO0129058 | 4/2001 |
| WO | WO0152843 | 7/2001 |
| WO | WO0164247 | 9/2001 |
| WO | WO0178698 | 10/2001 |
| WO | WO0192513 | 12/2001 |
| WO | WO0215924 | 2/2002 |
| WO | WO0217914 | 3/2002 |
| WO | WO0220479 | 3/2002 |
| WO | WO0220513 | 3/2002 |
| WO | WO0244321 | 6/2002 |
| WO | WO0296458 | 12/2002 |
| WO | WO02102232 | 12/2002 |
| WO | WO03022261 | 3/2003 |
| WO | WO2004026329 | 4/2004 |
| WO | WO2004028448 | 4/2004 |
| WO | WO2004032852 | 4/2004 |
| WO | WO2004032870 | 4/2004 |
| WO | WO2004058184 | 7/2004 |
| WO | WO2004065560 | 8/2004 |
| WO | WO2004073653 | 9/2004 |
| WO | WO2004096122 | 11/2004 |
| WO | WO2005000194 | 1/2005 |
| WO | WO2005019266 | 3/2005 |
| WO | WO2005111077 | 11/2005 |
| WO | WO2006077441 | 7/2006 |

OTHER PUBLICATIONS

American Chemical Society (1987-1991), *Chemical Abstracts, 12th Collective Index, Chemical Substances*, vols. 106-115, p. 34237CS, col. 3, lines 5-7.

American Chemical Society (1987-1991), *Chemical Abstracts, 12th Collective Index, Chemical Substances*, vols. 106-115, p. 34237CS, col. 3, lines 55-60.

American Chemical Society (1987-1991), *Chemical Abstracts, 12th Collective Index, Chemical Substances*, vols. 106-115, p. 34237CS, col. 3, lines 66-69.

American Chemical Society (1987-1991), *Chemical Abstracts, 12th Collective Index, Chemical Substances*, vols. 106-115, p. 34238CS, col. 1, lines 41-44.

American Chemical Society (1987-1991), *Chemical Abstracts, 12th Collective Index, Chemical Substances*, vols. 106-115, p. 34238CS, col. 2, lines 25-27.

American Chemical Society (1987-1991), *Chemical Abstracts, 12th Collective Index, Chemical Substances*, vols. 106-115, p. 34238CS, col. 2, lines 32-33.

American Chemical Society (1987-1991), *Chemical Abstracts, 12th Collective Index, Chemical Substances*, vols. 106-115, p. 34239CS, col. 3, lines 48-50.

American Chemical Society (1987-1991), *Chemical Abstracts, 12th Collective Index, Chemical Substances*, vols. 106-115, p. 34239CS, col. 3, lines 52-53.

Barbas III, C.F., et al., "In Vitro Evolution of a Neutralizing Human Antibody to Human Immunodeficiency Virus Type 1 to Enhance Affinity and Broaden Strain Cross-Reactivity", Proc. Natl. Acad. Sci., Apr. 1994, pp. 3809-3813, vol. 91.

Figure 2:
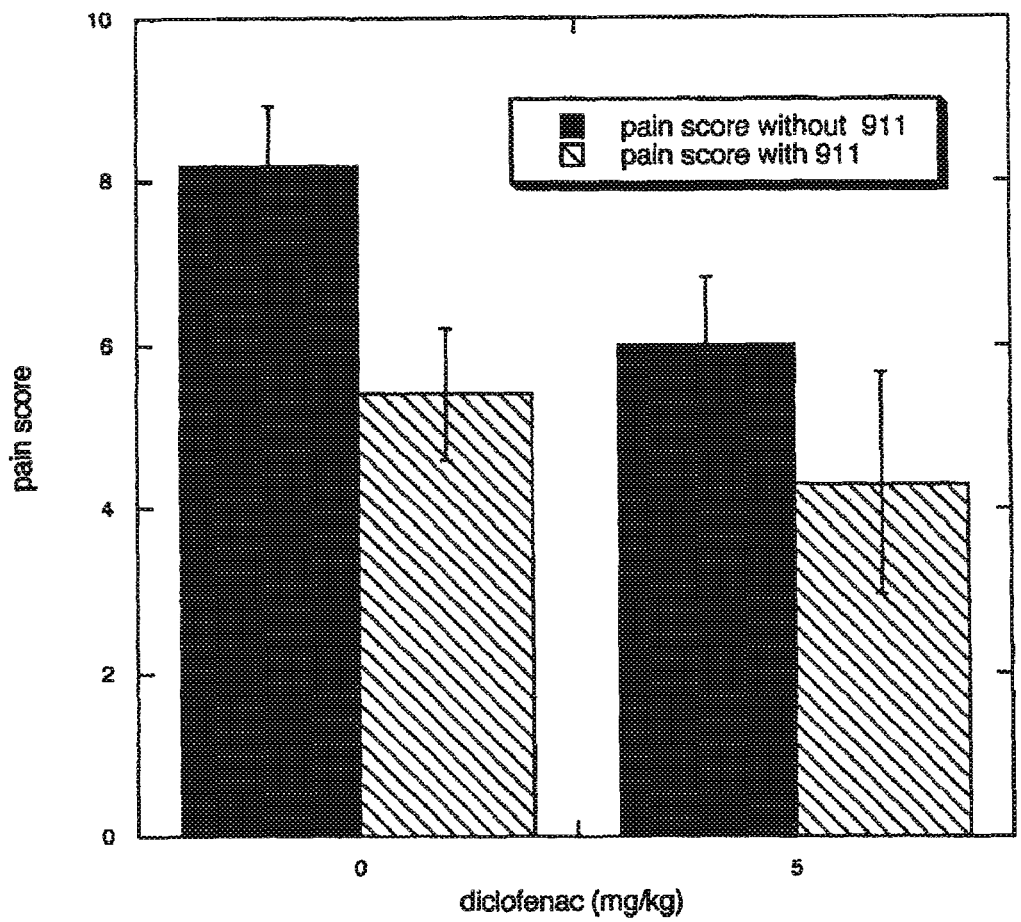

Barbas III, C.F., et al., "Vector pComb3X, Figure 2.2" *In* "Phage-Display Vectors" Chapter 2, *In* Phage Display: A Laboratory Manual, 2001, pp. 2.9-2.13, Cold Spring Harbor Laboratory Press, Cold Spring Harbor, NY.

Berzofsky, J.A., et al., "Immunogenicity and Antigen Structure", *In* Fundamental Immunology, 1993, Chapter 8, pp. 242, W.E. Paul, ed., Raven Press, NY, NY.

International Search Report for PCT Application No. PCT/US2006/013921, filed Apr. 11, 2006, mailed Jan. 2, 2007, seven pages.

Lane, N., et al., "RN624 (Anti-NGF) Improves Pain and Function in Subjects with Moderate Knee Osteoarthritis: A Phase 1 Study", Arthritis & Rheumatism, Sep. 2005, pp. S461, 52(9-Suppl.S), Abstract No. 1205.

Leem, J.W., et al., "Anti-NGF Treatment Suppresses Abnormal Pain Behaviors Induces After Spinal Cord Injury in the Rat", 30th Annual Meeting of the Society of Neuroscience, New Orleans, LA, Nov. 4-9, 2000, Society for Neuroscience Abstracts, 26(2):1690, Abstract No. 633.1.

Owolabi, J.B., et al., "Characterization of Antiallodynic Actions of ALE-0540, a Novel Nerve Growth Factor Receptor Antagonist in the Rat", J. Pharmacol. Exp. Ther., 1999, pp. 1271-1276, 289(3).

Sequence Alignments for Sequence Searches of SEQ ID Nos. 1-8, pp. 1-8, (2007).

Shelton, D.L., et al., "Nerve Growth Factor Mediates Hyperalgesia and Cachexia in Auto-Immune Arthritis", Pain, Jul. 2005, pp. 8-16, 116(1-2).

Supplementary European Search Report mailed Sep. 12, 2006, for EP Application No. 03779091.2 filed Oct. 3, 2003, four pages.

Vastag, B., "Monoclonals Expand into Neural Disorders", Nature Biotechnology, Jun. 2006, pp. 595-596, 24(6).

Banik, R.K., et al., "Anti-NGF Treatment Attenuates Spontaneous Pain and Thermal, but Not Mechanical Hyperalgesia, After Hind Paw Incision in the Rat", Society for Neuroscience, Nov. 12, 2003, Program No. 909.12, one page, Abstract Only.

International Search Report for PCT Application No. PCT/US03/32083, filed Oct. 8, 2003, mailed Mar. 4, 2005, three pages.

International Search Report for PCT Application No. PCT/US03/32083, filed Oct. 8, 2003, mailed May 17, 2004, three pages.

Peter, et al., CMAJ, 2001; 165: 12031209.

Sunshine, et al., Clin. Pharmacol Ther. 1987; 42; 374-380.

Kehlet, H., Ann Med., 1995; 27: 259-262.

Adey, N. B., et al., "Preparation of Second-Generation Phage Libraries", *In* Phage Display of Peptides and Proteins: A Laboratory Manual, 1996, Chapter 16, pp. 277-291. Kay, B.K., et al., eds. Academic Press Inc., San Diego, CA.

Kidd, B.L., et al., "Mechanisms of Inflammatory Pain", British J. of Anaesthesia, Jul. 2001, pp. 3-11, 87(1).

Amann, R., et al., "Inhibition of Carrageenan-Induced Edema by Indomethacin or Sodium Salicylate Does Not Prevent the . . . ", Neuroscience Letters, 2000, pp. 173-73, 278(3).

Hyllested, M., et la., "Comparative effect of paracetamol, Nsaids or their combination . . . ", British J. of Anaesthesia, 2002, pp. 199-214, 88(2).

Wideman, et al., "Analgesic efficacy of a combinational of hydrocodone with ibuprofen in postoperative pain", Clin. Pharmacology & Thera., 1999, pp. 66-76, 65(1).

Barkin, R.L., "Acetaminophen, Aspirin, or Ibuprofen in Combination Analgesic Products", American Journal of Therapeutics, 2001, pp. 433-442, 8(6).

Bellamy, N., "Pain Assessment in Osteoarthritis: Experience with the WOMAC Osteoarthritis Index", Semin. Arthritis Rheum., May 1989, pp. 14-17, 18(4 Suppl. 2).

Bellamy, N., et al., "Validation Study of WOMAC: A Health Status Instrument for Measuring Clinically Important Patient Relevant Outcomes to Antirheumatic Drug Therapy in Patients with Osteoarthritis of the Hip or Knee", J. Rheumatol., Dec. 1988, pp. 1833-1840, 15(12).

Bibel, M., et al., "Neurotrophins: Key Regulators of Cell Fate and Cell Shape in the Vertebrate Nervous System", Genes Dev., Dec. 1, 2000, pp. 2919-2937, 14(23).

Brennan, T.J., "Postoperative Models of Nociception", ILAR Journal, 1999, pp. 129-136, 40(3).

Brennan, T.J., et al., "Mechanisms of Incisional Pain", Anesthesiology Clin. N. Am., 2005, pp. 1-20, vol. 23.

Brosseau, L., et al., "Thermotherapy for Treatment of Osteoarthritis, The Cochrane Database of Systematic Reviews", 2003, pp. 1-20, Issue 4, Art No. CD004522.

Chaplan, S.R., et al., "Quantitative Assessment of Tactile Allodynia in the Rat Paw", J. Neuroscience Methods, 1994, pp. 55-63, vol. 53.

Chen, Y., et al., "Selection and Analysis of an Optimized Anti-VEGF Antibody: Crystal Structure of an Affinity-Matured Fab in Complex with Antigen", J. Mol. Biol., Nov. 5, 1999, pp. 865-881, 293(4).

Choi, S-S., et al., "Antinociceptive Mechanisms of Orally Administered Decursinol in the Mouse", Life Sciences, 2003, pp. 471-485, 73(4).

Clohisy, D.R., et al., "Skeletal Complications of Malignancy: Bone Cancer Pain", Clinical Orthopaedics and Related Research, 2003, pp. S279-S288, Vo. 415S.

Corey, E., et al., "Establishment and Characterization of Osseous Prostate Cancer Models: Intra-Tibial Injection of Human Prostate Cancer Cells", Prostate, Jun. 1, 2002, pp. 20-33, 52(1).

Cromartie, W.J., et al., "Arthritis in Rats After Systemic Injection of Streptococcal Cells or Cell Walls", The Journal of Experimental Medicine, 1997, pp. 1585-1602, vol. 146.

Dicou, E. et al., "Nerve Growth Factor (NGF) Autoantibodies and NGF in the Synovial Fluid: Implications if Spondylarthropathies", Autoimmunity, 1996, pp. 1-9-, 24(1).

Dicou, E., et al., "Increased Frequency of NGF in sera of Rheumatoid Arthritis and Systemic Lupus Erythematosus Patients", NeuroReport, Dec. 13, 1993, pp. 321-324, 5(3).

Dicou, E., et al., "Natural Autoantibodies Against the Nerve Growth Factor in Autoimmune Diseases", J. Neuroimmunol., Jan. 1994, pp. 224 (Erratum), 49(1).

Dicou, E., et al., "Evidence That Natural Autoantibodies Against the Nerve Growth Factor (NGF) May Be Potential Carriers of NGF", J. Neuroimmunol., May 1997, pp. 200-203, vol. 75.

Dicou, E., et al., "Natural Autoantibodies Against the Nerve Growth Factor in Autoimmune Diseases", J. Neuroimmunol., Sep. 1993, pp. 159-167, 47(2).

Edoff, K., et al., "Retrograde Tracing and Neuropeptide Immunohistochemistry of Sensory Neurones Projecting to the Cartilaginous Distal Femoral Epiphysis of Young Rats", Cell & Tissue Research, Feb. 2000, pp. 193-200, 299(2).

Fawcett, D.W., "Bone", *In* a textbook of Histology, Dreibelbis, D., ed., Eleventh Edition, W.B. Saunders Co., Philadelphia, PA, 1986, Chapter 8, pp. 211-216 and Table of Contents pp. v-xi.

Fischer, H.P., et al., "A Possible Role for Saliva as a Diagnostic Fluid in Patients with Chronic Pain", Semin. Arthritis Rheum., Jun. 1998, pp. 348-359, 27(6).

Fjell, J., et al., "In Vivo NGF Deprivation Reduces SNS Expression and TTX-R Sodium Currents in IB4-Negative DRG Neurons", J. Neurophysiol., Feb. 1999, pp. 803-810, 81(2).

Garcia-Castellano, J.M., et al., "Is Bone a Target-Tissue for the Nervous System? New Advances on the Understanding of Their Interactions", Iowa Orthop. J., 2000, pp. 49-58, vol. 20.

Garrett, N. E., et al., "Effect of Capsaicin on Substance P and Nerve Growth Factor in Adjuvant Arthritic Rats", Neurosci. Lett., Jul. 11, 1997, pp. 5-8, vol. 230.

Gavilondo, J.V., et al., "Antibody Engineering at the Millennium", Bio Techniques, Jul. 2000, pp. 128145, vol. 29.

GenBank Accession No. CAA09181, created Dec. 2, 1998, located at http://www.ncbi.nlm.nih.gov last visited Oct. 19, 2005, two pages.

GenBank Accession No. P01859, created Jul. 21, 1986, located at http://www.ncbi.nlm.nih.gov last.visited Oct. 19, 2005, four pages.

Greene, L.A., et al., "Establishment of a Noradrenergic Clonal Line of Rat Adrenal Pheochromocytoma Cells Which Respond to Nerve Growth Factor", Proc. Nat. Acad. Sci., Jul. 1976, pp. 2424-2428, 73(7).

Gwak, Y.S., et al., "Attenuation of Mechanical Hyperalgesia Following Spinal Cord Injury by Administration of Antibodies to Nerve Growth Factor in the Rat", Neuroscience Letters, Jan. 16, 2003, pp. 117-120, 33(2).

Halliday, D.A, et al., "Elevated Nerve Growth Factor Levels in the Synovial Fluid of Patients With Inflammatory Joint Disease", Neurochem. Res., Jun. 1998, pp. 919-922, 23(6).

Hasselström, J., et al., "Disposition and Analgesic Effects of Systemic Morphine, Morphine-6-glucuronide and Normorphine in Rat", Pharmacology & Toxicology, Jul. 1996, pp. 40-46, 79(1).

Haynes, M.K., et al., "Phenotypic Characterization of Inflammatory Cells From Osteoarthritic Synovium and Synovial Fluids", Clin. Immunol., Dec. 2002, pp. 315-325, 105(3).

Hill, R., "$Nk_1$ (Substance P) Receptor Antagonists—Why Are They Not Analgesic in Humans?", Trends Pharmacol. Sci., Jul. 2000, pp. 244-246, 21(7).

Honoré, P., et al., "Cellular and Neurochemical Remodeling of the Spinal Cord in Bone Cancer Pain", Prog. Brain Res., 2000, pp. 389-397, vol. 129.

Honoré, P., et al., "Osteoprotegerin Blocks Bone Cancer-Induced Skeletal Destruction, Skeletal Pain and Pain-Related Neurochemical Reorganization of the Spinal Cord", Nat. Med., May 2000, pp. 521-528, 6(5).

Honoré, P., et al., "Murine Models of Inflammatory, Neuropathic and Cancer Pain Each Generates a Unique Set of Neurochemical Changes in the Spinal Cord and Sensory Neurons", Neuroscience, Jun. 23, 2000, pp. 585-598, 98(3).

Honoré, P., et al., "Interleukin-$1\alpha\beta$ Gene-Deficient Mice Show Reduced Nociceptive Sensitivity in Models of Inflammatory and Neuropathic Pain but not Post-Operative Pain", Behavioural Brain Research, 2006, pp. 355-364, vol. 167.

Huang, E.J., et al., "Neurotrophins: Roles in Neuronal Development and Function", Annu. Rev. Neurosci., 2001, pp. 677-736, vol. 24.

Hunt, S.P., et al., "Induction of c-fos-like Protein in Spinal Cord Neurons Following Sensory Stimulation", Nature, Aug. 13, 1987, pp. 632-634, vol. 328.

Huse, W.D., et al., "Increased Antibody Affinity and Specificity by Codon-Based Mutagenesis", Intern. Rev. Immunol., 1993, pp. 129-137, vol. 10.

Iadarola, M.J., et al., "Differential Activation of Spinal Cord Dynorphin and Enkephalin Neurons During Hyperalgesia: Evidence Using cDNA Hybridization", Brain Res., 1988, pp. 205-212, 455(2).

International Search Report for PCT Application No. PCT/US03/32113, filed Oct. 8, 2003, mailed Apr. 10, 2006, four pages.

International Search Report for PCT Application No. PCT/US04/05162, filed Feb. 19, 2004, mailed Mar. 28, 2006, four pages.

International Search Report for PCT Application No. PCT/US2005/011786, filed Apr. 7, 2005, mailed Feb. 20, 2006, five pages.

Jongen, J.L.M., et al., "Neurotrophic Factors and Cancer Pain: The Expression of NGF, GDNF and BDNF by the Murine Osteolytic Sarcoma Cell Line 2472 in vitro and in vivo and Their Potential Involvement in Bone Cancer Pain", 32nd Annual Meeting of the Society for Neuroscience, Orlando, FL, (Nov. 2-7, 2002), Abstract 52.2, located at http://sfn.scholarone.com/iten2002/main/html, last visited Mar. 2, 2006, two pages.

Kasai, M., et al., "Endogenous Nerve Growth Factor Increases the Sensitivity to Bradykinin in Small Dorsal Root Ganglion Neurons of Adjuvant Inflamed Rats", Neuroscience Letters, 1999, pp. 41-44, 272(1).

Kazemier, B., et al., "Determination of Active Single Chain Antibody Concentrations in Crude Periplasmic Fractions", J. Immunol. Methods, 1996, pp. 201-209, 194(2).

Lewin, G.R., et al., "Nerve Growth Factor-Induced Hyperalgesia in the Neonatal and Adult Rat", J. Neurosci., May 1993, pp. 2136-2148, 13(5).

Luger, N. M., et al., "Osteoprotegerin Diminishes Advanced Bone Cancer Pain", Cancer Res., May 15, 2001, pp. 4038-4047, vol. 61.

Luger, N. M., et al., "Efficacy of Systemic Morphine Suggests a Fundamental Difference in the Mechanisms that Generate Bone Cancer vs. Inflammatory Pain", Pain, 2002, pp. 397-406, vol. 99.

Mach, D.B., et al., "Origins of Skeletal Pain: Sensory and Sympathetic Innervation of the Mouse Femur", Neuroscience, 2002, pp. 155-166, 113(1).

Mantyh, P.W., et al., "Molecular Mechanisms of Cancer Pain", Nature Reviews Cancer, Mar. 2002, pp. 201-209, 2(3).

McCarthy, B.G., et al., "Cutaneous Innervation in Sensory Neuropathies", Neurology, Oct. 1995, pp. 1848-1855, 45(10).

McDonald, N. Q., et al., "New Protein Fold Revealed by a 2.3-A Resolution Crystal Structure of Nerve Growth Factor", Nature, Dec. 5, 1991, pp. 411-414, vol. 354.

McMahon, S.B., "The Biological Effects of Endogenous Nerve Growth Factor on Adult Sensory Neurons Revealed by a trkA-IgG Fusion Molecule", Nature Medicine, Aug. 1995, pp. 774-780, 1(8).

McMahon, S.B., "NGF as a Mediator of Inflammatory Pain", Phil Trans. R. Soc. Land. B., Mar. 29, 1996, pp. 431-440, 351(1338).

Molander, C., et al., "Spinal Cord Projections From Hindlimb Muscle Nerves in the Rat Studied by Transganglionic Transport of Horseradish Peroxidase, Wheat Germ Agglutinin Conjugated Horseradish Peroxidase, or Horseradish Peroxidase With Dimethylsulfoxide", J. Comp. Neurol., Jun. 8, 1987, pp. 246-255, 260(2).

Muller, Y.A., et al., VEGF and the Fab Fragment of a Humanized Neutralizing Antibody: Crystal Structure of the Complex a 2.4A Resolution and Mutational Analysis of the Interface, Structure, 1998, pp. 1153-1167, 6(9).

Muyldermans, S., "Single Domain Camel Antibodies: Current Status", Reviews in Molecular Biotechnology, 2001, pp. 277-302, vol. 74.

Myers, R.R., et al., "Reduced Hyperalgesia in Nerve-Injured WLD Mice: Relationship to Nerve Fiber Phagocytosis, Axonal Degeneration, and Regeneration in Normal Mice", Exp. Neurol., Sep. 1996, pp. 94-101, 141(1).

Niissalo, S., et al., "Neuropeptides in Experimental and Degenerative Arthritis", Ann. N. Y. Acad. Sci., Jun. 2002, pp. 384-399, vol. 966.

Noguchi, K., et al., "Dynorphin Expression and Fos-like Immunoreactivity Following Inflammation Induced Hyperalgesia are Colocalized in Spinal Cord Neurons", Molecular Brain Research, 1991, pp. 227-233, 10(3).

Pezet, S., et al., "Differential Regulation of NGF Receptors in Primary Sensory Neurons by Adjuvant-Induced Arthritis in the Rat", Pain, Feb. 1, 2001, pp. 113-125, 90(1-2).

Pozza, M., et al., "A Histochemical Study of the Rheumatoid Synovium: Focus on Nitric Oxide, Nerve Growth Factor High Affinity Receptor, and Innervation", J. Rheumatol., May 2000, pp. 1121-1127, 27(5).

Puigdellivol-Sánchez, A., et al., "Sciatic and Femoral Nerve Sensory Neurones Occupy Different Regions of the L4 Dorsal Root Ganglion in the Adult Rat", Neurosci. Lett., 1998, pp. 169-172, 251(3).

Puigdellivol-Sánchez, A., et al., "Contribution of Femoral and Proximal Sciatic Nerve Branches to the Sensory Innervation of Hindlimb Digits in the Rat", The Anatomical Record, Oct. 1, 2000, pp. 180-188, 260(2).

Rader, C., et al., "Antibody Engineering", In Phage Display, A Laboratory Manual, Barbas III, C.F., et al., eds., Cold Spring Harbor, NY, 2001, pp. 13.1-13.15. Chapter 13.

Rinat Neurosciences. (Date Unknown). "RN624 A New Approach to Pain Therapy", located at http://64.233.161.104/search?q=cache:nYXEK1HDbdIJ:www.rinatneuro.com/products/RN6, last visited Jul. 5, 2006, five pages.

Rosok, M.J., et al., "A Combinatorial Library Strategy for the Rapid Humanization of Anticarcinoma BR96 Fab", The Journal of Biological Chemistry, Sep. 13, 1996, pp. 22611-22618, 271(37).

Rudikoff, S., et al., "Single Amino Acid Substitution Altering Antigen-Binding Specificity", Proc. Natl. Acad. Sci., Mar. 1982, pp. 1979-1983, vol. 79.

Sabino, M.A.C., et al., "Simultaneous Reduction in Cancer Pain, Bone Destruction, and Tumor Growth by Selective Inhibition of Cyclooxygenase-2", Cancer Res., Dec. 15, 2002, pp. 7343-7349, vol. 62.

Sabino, M.A.C., et al., "Different Tumors in Bone Each Give Rise to a Distinct Pattern of Skeletal Destruction, Bone Cancer-Related Pain Behaviors and Neurochemical Changes in the Central Nervous System", International Journal of Cancer, May 1, 2003, pp. 550-558, 104(5).

Safieh-Garabedian, B, et al., "Contribution of Interleukin-1β to the Inflammation-Induced Increase in Nerve Growth Factor Levels and Inflammatory Hyperalgesia", Br. J. Pharmacol., Aug. 1995, pp. 1265-1275, 115(7).

Schwei, M.J., et al., "Neurochemical and Cellular Reorganization of the Spinal Cord in a Murine Model of Bone Cancer Pain", J. Neuroscience, Dec. 15, 1999, pp. 10886-10897, 19(24).

Shelton, D.L., et al., "Expression of the β-nerve Growth Factor Gene Correlates with the Density of Sympathetic Innervation in Effector Organs", Proc. Natl. Acad. Sci., Dec. 1984, pp. 7951-7955, vol. 81.

Shelton, D.L., et al., "Neurotrophins and Neurotrophin Antagonists as Potential Therapeutics", Restorative Neurology and Neuroscience, 1995, pp. 99-100, 8(1-2).

Shu, X., et al., "Nerve Growth Factor Acutely Sensitizes the Response of Adult Rat Sensory Neurons to Capsaicin", Neurosci. Lett.,1999, pp. 159-162, 274(3).

Stedman, T.L., (1982), Illustrated Stedman's Medical Dictionary, Williams & Wilkins: Baltimore, MD, 24th Edition, p. 670.

Sunshine, A., et al., "Oral Analgesic Efficacy of Suprofen Compared to Aspirin, Aspirin plus Codeine, and Placebo in Patients with Postoperative Dental Pain", Pharmacology, 1983, pp. 31-40, 27(Suppl. 1).

Szekanecz, Z, et al., "Temporal Expression of Inflammatory Cytokines and Chemokines in Rat Adjuvant-Induced Arthritis", Arthritis & Rheumatism, Jun. 2000, pp. 1266-1277, 43(6).

Tang, Y., et al., "Use of a Peptide Mimotope to Guide the Humanization of MRK-16, an Anti-P-Glycoprotein Monoclonal Antibody", The Journal of Biological Chemistry, Sep. 24, 1999, pp. 27371-27378, 274(39).

Thompson, J.E., et al., "A Fully Human Antibody Neutralising Biologically Active Human TGFβ2 for use in Therapy", J. Immunol. Methods, 1999, pp. 17-29, vol. 227.

Tofaris, G.K., et al., "Denervated Schwann Cells Attract Macrophages by Secretion of Leukemia Inhibitory Factor (LIF) and Monocyte Chemoattractant Protein-1 in a Process Regulated by Interleukin-6 and LIF", J. Neurosci., Aug. 1, 2002, pp. 6696-6703, 22(15).

Tsujino, H., et al., "Activating Transcription Factor 3 (ATF3) Induction by Axotomy in Sensory and Motoneurons: A Novel Neuronal Marker of Nerve Injury", Molecular & Cellular Neuroscience, Feb. 2000, pp. 170-182, 15(2).

Vajdos, F.F., et al., "Comprehensive Functional Maps of the Antigen-Binding Site of an Anti-ErbB2 Antibody Obtained with Shotgun Scanning Mutagenesis", J. Mol. Biol., 2002, pp. 415-428, vol. 320.

Vanderah, T.W., et al., "Mechanisms of Opioid-Induced Pain and Antinociceptive Tolerance: Descending Facilitation and Spinal Dynorphin", Pain, 2001, pp. 5-9, vol. 92.

Vigneti, E., et al., "Production and Characterization of a Monoclonal Antibody Against Nerve Growth Factor (NGF) Which Recognizes Rodent and Human NGF", Year Immunol., 1993, pp. 146-149, vol. 7.

Villanueva, L., "Is There a Gap Between Preclinical and Clinical Studies of Analgesia?", Trends Pharmacol. Sci., Dec. 2000, pp. 461-465, 21(12).

Wiesmann, C., et al., "Crystal Structure of Nerve Growth Factor in Complex with the Ligand-Binding Domain of the TrkA Receptor", Nature, Sep. 9, 1999, pp. 184-188, 401(6749).

Winter, C.A., et al., "Treatment of Adjuvant Arthritis in Rats with Anti-inflammatory Drugs", Arthritis Rheum., Jun. 1966, pp. 394-404, 9(3).

Woolf, C.J., et al., "Nerve Growth Factor Contributes to the Generation of Inflammatory Sensory Hypersensitivity", Neuroscience, 1994, pp. 327-331, 62(2).

Wu, H., et al., "Humanization of a Murine Monoclonal Antibody by Simultaneous Optimization of Framework and CDR Residues", J. Mol. Biol., Nov. 19, 1999, pp. 151-162, 294(1).

Wu, S.M., et al., "Oxidized $\alpha_2$-Macroglobulin ($\alpha^2$M) Differentially Regulates Receptor Binding by Cytokines/Growth Factors: Implication for Tissue Injury and Repair Mechanisms in Inflammation", The Journal of Immunology, 1998, pp. 4356-4365, vol. 161.

Wu, Z, et al., "Immunohistochemical Study of NGF and its Receptors in the Synovial Membrane of the Ankle Joint of Adjuvant-Induced Arthritic Rats", Histochem. Cell Biol., Dec. 2000, pp. 453-459, 114(6).

Yelton, D.E., et al., "Affinity Maturation of the BR96 Anti-Carcinoma Antibody Codon-Based Mutagenesis", The Journal of Immunology, 1995, pp. 1994-2004, vol. 155.

Yu, Y.C., et al., "Two Variables That can be Used as Pain Indices in Experimental Animal Models of Arthritis", Journal of Neuroscience Methods, 2002, pp. 107-113, vol. 115.

Zahn, P.K., et al., "Mechanisms for Pain Caused by Incisions", Regional Anesthesia and Pain Medicine, Sep.-Oct. 2002, pp. 514-516, 27(5).

Zahn, P.K., et al., "Effect of Blockade of Nerve Growth Factor and Tumor Necrosis Factor on Pain Behaviors After Plantar Incision", The Journal of Pain, Apr. 2004, pp. 157-163, 5(3).

Agrawal, S., et al., "Mixed Backbone Oligonucleotides: Improvement in Oligonucleotide-Induced Toxicity In Vivo", Antisense & Nucleic Acid Drug Development, 1998, pp. 135-139, vol. 8.

Aley, K.O., et al., "Delayed Sympathectomy After a Prolonged Hyperalgesia Results in a Subsequent Enhanced Acute Hyperalgesic Response", Neuroscience, 1996, pp. 1083-1090, 71(4).

Al-Lazikani, B., et al., "Standard Conformations for the Canonical Structures of Immunoglobulins", J. Molec. Biol., 1997, pp. 927-948, vol. 273.

Aloe, L., et al., "Nerve Growth Factor and Distribution of Mast Cells in the Synovium of Adult Rats", Clin. Exp. Rheumatol., 1992, pp. 203-204, vol. 10.

Aloe, L., et al., "Nerve Growth Factor in the Synovial Fluid of Patients with Chronic Arthritis", Arch. Rheum., 1992, pp. 351-355, 35(3).

Aloe, L., et al., "Level of Nerve Growth Factor and Distribution of Mast Cells in the Synovium of Tumour Necrosis Factor Transgenic Arthritic Mice", Int. J. Tissue Reactions, 1993, pp. 139-143, 15(4).

Aloe, L., et al., "Effect of NGF Antibodies on Mast Cell Distribution, Histamine and Substance P Levels in the Knee Joint of TNF-Arthritic Transgenic Mice", Rheumatol. Int., 1995, pp. 249-252, vol. 14.

Amann, R., et al., "Intraplantar Injection of Nerve Growth Factor into the Rat Hind Paw: Local Adema and Effects on Thermal Nociceptive Threshold", Pain, 1996, pp. 323-329, vol. 64.

Andreev, N. Y., et al., "Peripheral Administration of Nerve Growth Factor in the Adult Rat Produces a Thermal Hyperalgesia that Requires the Presence of Sympathetic Post-Ganglionic Neurones", Pain 1995, pp. 109-115, vol. 63.

Apfel, S.C., et al., "Nerve Growth Factor Regulates the Expression of Brain-Derived Neurotrophic Factor mRNA in the Peripheral Nervous System", Mol. Cell. Neurosci., 1996, pp. 134-142, vol. 7.

Armour, K.L., et al., "Recombinant Human IgG Molecules Lacking Fcγ Receptor I Binding and Monocyte Triggering Activities", Eur. J. Immunol., 1999, pp. 2613-2624, vol. 29.

Balint, R.F., et al., "Antibody Engineering by Parsimonious Mutagenesis", Gene, 1993, pp. 109-118, vol. 137.

Bird, R.E., et al., "Single-Chain Antigen-Binding Proteins", Science, 1988, pp. 423-426, vol. 242.

Bischoff, S.C., et al., "Effect of Nerve Growth Factor on the Release of Inflammatory Mediators by Mature Human Basophils", Blood, 1992, pp. 2662-2669, 79(10).

Boerner, P., et al., "Production of Antigen-Specific Human Monoclonal Antibodies From In Vitro-Primed Human Splenocytes", J. Immunol., 1991, pp. 86-95, 147(1).

Boettger, M.K., et al., "Calcium-Activated Potassium Channel SK1- and IK1-like Immunoreactivity in Injured Human Sensory Neurones and its Regulation by Neurotrophic Factors", Brain, 2002, pp. 252-263, vol. 125.

Borsani, G., et al., "cDNA Sequence of Human β-NGF", Nuc. Acids Res., 1990, pp. 4020, 18(13).

Boyd, P.N., et al., "The Effect of the Removal of Sialic Acid, Galactose and Total Carbohydrate on the Functional Activity of Campath-1H", Mol. Immunol., 1996, pp. 1311-1318, 32(17/18).

Bracci-Laudiero, L., et al., "Multiple Sclerosis Patients Express Increased Levels of β-Nerve Growth Factor in Cerebrospinal Fluid", Neurosci. Lett., 1992, pp. 9-12, vol. 147.

Bracci-Laudiero, L., et al., "Increased Levels of NGF in Sera of Systemic Lupus Erythematosus Patients", Neuroreport, 1993, pp. 563-565, 4(5).

Braun, A., et al., "Role of Nerve Growth Factor in a Mouse Model of Allergic Airway Inflammation and Asthma", Eur. J. Immunol., 1998, pp. 3240-3251, vol. 28.

Brennan, T.J., et al., "Characterization of a Rat Model of Incisional Pain", Pain, 1996, pp. 493-501, vol. 64.

Brennan, T.J., et al., "Role of Nerve Growth Factor in a Rat Model for Postoperative Pain", Society for Neuroscience Abstracts, 28th Annual Meeting, Los Angeles, CA, Nov. 7-12, 1998, pp. 880, 24(1), Abstract No. 349.4.

Brown, B.A., et al., "Tumor-Specific Genetically Engineered Murine/Human Chimeric Monoclonal Antibody", Cancer Res., 1987, pp. 3577-3583, vol. 47.

Buchman, V.L., et al., "Different Neurotrophins are Expressed and Act in a Developmental Sequence to Promote the Survival of Embryonic Sensory Neurons", Development, 1993, pp. 989-1001, vol. 118.

Buck, D.W., et al., "Monoclonal Antibodies Specific for Cell Culture Mycoplasmas", In Vitro, 1982, pp. 377-381, 18(4).

Capel, P.J.A., et al., "Heterogeneity of Human IgG Fc Receptors", Immunomethods, 1994, pp. 25-34, vol. 4.

Caraceni, A., et al., "Pain Measurement Tools and Methods in Clinical Research in Palliative Care: Recommendations of an Expert Working Group of the European Association of Palliative Care", J. Pain Symptom. Manage., 2002, pp. 239-255, 23(3).

Chao, M.V., et al., "Gene Transfer and Molecular Cloning of the Human NGF Receptor", Science, 1986, pp. 518-521, vol. 232.

Chiou, H.C., et al., "In Vivo Gene Therapy via Receptor-Mediated DNA Delivery", In Gene Therapeutics: Methods and Applications of Direct Gene Transfer, 1994, J.A. Wolff, ed. Birkhauser, pp. 143-156.

Chothia, C., et al., "Conformations of Immunoglobulin Hypervariable Regions", Nature, 1989, pp. 877-883, vol. 342.

Chuang, H.H., et al., "Bradykinin and Nerve Growth Factor Release the Capsaicin Receptor from PtdIns(4,5)$P_2$-Mediated Inhibition", Nature, 2001, pp. 957-962, vol. 411.

Chun, L.L.Y., et al., "Role of Nerve Growth Factor in the Development of Rat Sympathetic Neurons in Vitro", The Journal of Cell Biology, 1977, pp. 705-711, vol. 75.

Clackson, T., et al., "Making Antibody Fragments Using Phage Display Libraries", Nature, 1991, pp. 624-628, vol. 352.

Clynes, R., et al., "Fc Receptors Are Required in Passive and Active Immunity to Melanoma", Proc. Natl. Acad. Sci., 1998, pp. 652-656, vol. 95.

Cole, S.P.C., et al., "The EBV-Hybridoma Technique and Its Application to Human Lung Cancer", In Monoclonal Antibodies and Cancer Therapy, 1985, Reisfeld, R., et al., eds., Alan R. Liss, Inc., New York, NY, pp. 77-96.

Connelly, S., et al., "In Vivo Gene Delivery and Expression of Physiological Levels of Functional Human Factor VIII in Mice", Human Gene Therapy 1995, pp. 185-193, vol. 6.

Crowley, C., et al., "Mice Lacking Nerve Growth Factor Display Perinatal Loss of Sensory and Sympathetic Neurons yet Develop Basal Forebrain Cholinergic Neruons", Cell, 1994, pp. 1001-1011, vol. 76.

Curiel, D.T., et al., "High-Efficiency Gene Transfer Mediated by Adenovirus Coupled to DNA-Polylysine Complexes", Hum. Gene Ther., 1992, pp. 147-154, vol. 3.

Daugherty, B.L., et al., "Polymerase chain Reaction Facilitates the Cloning, CDR-Grafting, and Rapid Expression of a Murine Monoclonal Antibody Directed Against the CD18 Component of Leukocyte Integrins", Nucl. Acids Res., 1991, pp. 2471-2476, 19(9).

Dayhoff, M.O., ed. (1978), "A Model of Evolutionary Change in Proteins", In Atlas of Protein Sequence and Structure, National Biomedical Research Foundation, Washington, D.C., Chapter 22, pp. 345-352, 5(Supp. 3).

deHaas, M., et al., "Fcγ Receptors of Phagocytes", J. Lab. Clin. Med., 1995, pp. 330-341, vol. 126.

DeKock, M., et al., "Balanced Analgesia in the Perioperative Period: Is There a Place for Ketamine?", Pain, 2001, p. 373-380, vol. 92.

DiMarco, E., et al., "Nerve Growth Factor Binds to Normal Human Keratinocytes Through High and Low Affinity Receptors and Stimulates Their Growth by a Novel Autocrine Loop", J. Biol. Chem., 1993, pp. 22838-22846, 268(30).

Dyck, P.J., et al. "Intradermal Recombinant Human Nerve Growth Factor Induces Pressure Allodynia and Lowered Heat-Pain Threshold in Humans", Neurology, 1997, pp. 501-505, vol. 48.

Eide, F.F., et al., "Naturally Occurring Truncated trkB Receptors Have Dominant Inhibitory Effects on Brain-Derived Neurotrophic Factor Signaling", J. Neurosci., 1996, pp. 3123-3129, 16(10).

Eppstein, D.A., et al., "Biological Activity of Liposome-Encapsulated Murine Interferon γ is Mediated by a Cell Membrane Receptor", Proc. Natl. Acad. Sci., 1985, pp. 3688-3692, vol. 82.

Falcini, F., et al., "Increased Circulating Nerve Growth Factor is Directly Correlated with Disease Activity in Juvenile Chronic Arthritis", Ann. Rheum. Dis., 1996, pp. 745-748, vol. 55.

Felson, D.T., et al., "The American College of Rheumatology Preliminary Core Set of Disease Activity Measures for Rheumatoid Arthritis Clinical Trial", Arthritis and Rheumatism, 1993, pp. 729-740, 36(6).

Findeis, M.A., et al., "Targeted Delivery of DNA for Gene Therapy Via Receptors", Trends Biotechnol., 1993, pp. 202-205, vol. 11.

Foster, P.A., et al., "Cellular Pathology Changes in Rat Skin Following Intradermal Injection of Nerve Growth Factor: Neutrophil-Dependent and -Independent Events", J. Pathol. 2002, pp. 245-255, vol. 197.

Fries, J.F., et al., "The Dimensions of Health Outcomes: The Health Assessment Questionnaire, Disability and Pain Scales", J. Rheumatol., 1982, pp. 789-793, 9(5).

Gazzano-Santoro, H., et al., "A Non-Radioactive Complement-Dependent Cytotoxicity Assay for Anti-CD20 Monoclonal Antibody", J. Immunol. Methods, 1996, pp. 163-171, vol. 202.

GenBank Accession No. L17077, "The Use of the RACE Method to Clone Hybridoma cDNA When V Region Primers Fail", created on Feb. 7, 1995, located at http://www.ncbi.nih.gov , last visited on Mar. 18, 2004, two pages.

GenBank Accession No. L17078, "The Use of the RACE Method to Clone Hybridoma cDNA When V Region Primers Fail", created on Feb. 7, 1995, located at http://www.ncbi.nih.gov , last visited on Mar. 18, 2004, one page.

GenBank Accession No. NM_002506, "Histamine Enhances the Production of Nerve Growth Factor in Human Keratinocytes", created on Dec. 23, 2003, located at http://www.ncbi.nig.gov , last visited on Jun. 11, 2004, four pages.

GenBank Accession No. U39608, "Two Distinct Monoclonal Antibodies Raised Against Mouse Beta Nerve Growth Factor: Generation of Bi-Specific Anti-Nerve Growth Factor Anti-Horseradish Peroxidase Antibodies for Use in a Homogenous Enzyme Immunoassay", created on Mar. 25, 1999, located at http://www.ncbi.nih.gov, last visited on Mar. 18, 2004, two pages.

GenBank Accession No. U39609, "Two Distinct Monoclonal Antibodies Raised Against Mouse Beta Nerve Growth Factor: Generation of Bi-Specific Anti-Nerve Growth Factor Anti-Horseradish Peroxidase Antibodies for Use in a Homogenous Enzyme Immunoassay", created on Jan. 28, 1999, located at http://www.ncbi.nih.gov, last visited on Mar. 18, 2004, two pages.

Gerstenfeld, L.C., et al., "Differential Inhibition of Fracture Healing by Non-Selective and Cyclooxygenase-2 Selective Non-Steroidal Anti-Inflammatory Drugs", J. Orthop. Res., 2003, pp. 670-675, vol. 21.

Gould, H.J., III, et al., "A Possible Role for Nerve Growth Factor in the Augmentation of Sodium Channels in Models of Chronic Pain", Brain Res., 2000, pp. 19-29, vol. 854.

Griffiths, A.D., et al., "Human Anti-Self Antibodies with High Specificity From Phage Display Libraries", EMBO J., 1993, pp. 725-734, 12(2).

Guyer, R.L., et al., "Immunoglobulin Binding by Mouse Intestinal Epithelial Cell Receptors", J. Immunol., 1976, pp. 587-593, 117(2).

Hains, B.C, et al., "Differential Electrophysiological Effects of Brain-Derived Neurotrophic Factor on Dorsal Horn Neurons Following Chronic Spinal Cord Hemisection Injury in the Rat", Neurosci. Lett., 2002, pp. 125-128, vol. 320.

Haws, M.J., et al., "The Effects of Chronic Ketorolac Tromethamine (Toradol) on Wound Healing", Ann. Plas. Surg., 1996, pp. 147-151, vol. 37.

Hein, J., "Unified Approach to Alignment and Phylogenes", In Methods in Enzymology, 1990, Academic Press, Inc., San Diego, CA, Chapter 39, pp. 626-645, vol. 183.

Higgins, D.G., et al., "Fast and Sensitive Multiple Sequence Alignments on a Microcomputer", CABIOS Communications, 1989, pp. 151-153, 5(2).

Higuchi, R., "Recombinant PCR", In PCR Protocols: A Guide to Methods and Application, 1990, Innis, M.A., eta I., eds., Academic Press, Inc., Chapter 22, pp. 177-183.

Holliger, P., et al., "'Diabodies': Small Bivalent and Bispecific Antibody Fragments", Proc. Natl. Acad. Sci., 1993, pp. 6444-6448, vol. 90.

Hongo, J.S., et al., "Antibody Binding Regions on Human Nerve Growth Factor Identified by Homologand Alanine-Scanning Mutagenesis", Hybridoma, 2000, pp. 215-227, 19(3).

Hoogenboom, H.R., et al., "By-Passing Immunisation: Human Antibodies From Synthetic Repertoires of Germline $V_H$ Gene Segments Rearranged in Vitro", J. Mol. Biol., 1991, pp. 381-388, vol. 227.

Horigome, K., et al., "Mediator Release from Mast Cells by Nerve Growth Factor", J. Biol. Chem., 1993, pp. 14881-14887, 268(20).

Hsu, T-A., et al., "Differential N-Glycan Patterns of Secreted and Intracellular IgG Produced in *Trichoplusia ni* Cells", J. Biol. Chem., 1997, pp. 9062-9070, 272(14).

Hwang, K.J., et al., "Hepatic Uptake and Degradation of Unilamellar Sphingomyelin/Cholesterol Liposomes: A Kinetic Study", Proc. Natl. Acad. Sci., 1980, pp. 4030-4034, 77(7).

Iannone, F., et al., "Increased Expression of Nerve Growth Factor (NGF) and High Affinity NGF Receptor (p140 TrkA) in Human Osteoarthritic Chondrocytes", Rheumatology, 2002, pp. 1413-1418, vol. 41.

Jefferis, R., et al., "Glycosylation of Antibody Molecules: Structural and Functional Significance", Chem. Immunol., 1997, pp. 111-128, vol. 65.

Johnson, K.S., et al., "Human Antibody Engineering", Current Opinion in Structural Biology, 1993, pp. 564-571, vol. 3.

Jolly, D., "Viral Vector Systems for Gene Therapy", Cancer Gene Therapy, 1994, pp. 51-64, 1(1).

Jones, P.T., et al., "Replacing the Complementarity-Determining Regions in a Human Antibody with Those from a Mouse", Nature, 1986, pp. 522-525, vol. 321.

Kabat, E.A., et al., "Sequences of Proteins of Immunological Interest", Fifth Edition, National Institutes of Health: Bethesda, MD, 1991, pp. iii-xi (Table of Contents Only).

Kaplitt, M.G., et al., "Long-Term Gene Expression and Phenotypic Correction Using Adeno-Associated Virus Vectors in the Mammalian Brain", Nature Genetics, 1994, pp. 148-153, vol. 8.

Karlsson, R., et al., "Kinetic and Concentration Analysis Using BIA Technology", Methods: A Companion to Methods in Enzymology, 1994, Academics Press, Inc., pp. 99-110, vol. 6.

Kassel, O., et al., "Local Increase in the Number of Mast Cells and Expression of Nerve Growth Factor in the Bronchus of Asthmatic Patients After Repeated Inhalation of Allergen at Low-Dose", Clin. Exp. Allergy, 2001, pp. 1432-1440, vol. 31.

Katz, J., et al., "Measurement of Pain", Surg. Clin. North Am., 1999, pp. 231-252, 79(2).

Kawamoto, K., et al., "Nerve Growth Factor Activates Mast Cells Through the Collaborative Interaction with Lysophosphatidylserine Expressed on the Membrane Surface of Activated Platelets", J. Immunol., 2002, pp. 6412-6419, vol. 168.

Kerr, B.J., et al., "A Role for the TTX-Resistant Sodium Channel Nav 1.8 in NGF-Induced Hyperalgesia, But Not Neuropathic Pain", Neuroreport, 2001, pp. 3077-3078, 12(14).

Kim, J-K., et al., "Localization of the Site of Murine IgG1 Molecule that is Involved in Binding to the Murine Intestinal Fc Receptor", Eur. J. Immunol., 1994, pp. 2429-2434, vol. 24.

Kimura, O., et al., "Retroviral Delivery of DNA into the Livers of Transgenic Mice Bearing Premalignant and Malignant Hepatocellular Carcinomas", Human Gene Therapy, 1994, pp. 845-852, vol. 5.

Klein, R., et al., "The *trk*B Tyrosine Protein Kinase Gene Codes for a Second Neurogenic Receptor that Lacks the Catalytic Kinase Domain", Cell, 1990, pp. 647-656, vol. 61.

Knüsel, B., et al., "K-252b Is a Selective and Nontoxic Inhibitor of Nerve Growth Factor Action on Cultured Brain Neurons", J. Neurochemistry, 1991, pp. 955-962, vol. 57.

Knüsel, B., et al., "K-252b Selectively Potentiates Cellular Actions and *trk* Tyrosine Phosphorylation Mediated by Neurotrophin-3", J. Neurochemistry, 1992, pp. 715-722, vol. 59.

Kohler, B., et al., "Continuous Cultures of Fused Cells Secreting Antibody of Predefined Specificity", Nature, 1975, pp. 495-497, vol. 256.

Koizumi, S., et al., "K-252a: A Specific Inhibitor of the Action of Nerve Growth Factor of PC12 Cells", J. Neuroscience, 1988, pp. 715-721, 8(2).

Kuzuan, S., et al., "Evaluation of Analgesic Agents in Rats with Adjuvant Arthritis", Chem. Pharm. Bull., 1975, pp. 1184-1191, vol. 23.

Lamballe, F., et al., "*trk*C Encodes Multiple Neurotrophin-3 Receptors with Distinct Biological Properties and Substrate Specificities", EMBO J., 1993, pp. 3083-3094, 12(8).

Lambiase, A., et al., "Clinical Application of Nerve Growth Factor on Human Corneal Ulcer", Arch. Ital. Biol., 2003, pp. 141-148, vol. 141.

Leon, A., et al., "Mast Cells Synthesize, Store, and Release Nerve Growth Factor", Proc. Natl. Acad. Sci., 1994, pp. 3739-3743, vol. 91.

Levi-Montalcini, R., et al., "Nerve Growth Factor", Physiol. Rev., 1968, pp. 534-569, 48(3).

Lewin, G.R., et al., "Peripheral and Central Mechanisms of NGR-Induced Hyperalgesia", European Journal of Neuroscience, 1994, pp. 1903-1912, vol. 6.

Li, Y-X, et al., "Expression of a Dominant Negative TrkB Receptor, T1, Reveals a Requirement for Presynaptic Signaling in BDNF-Induced Synaptic Potentiation in Cultured Hippocampal Neurons", Proc. Natl. Acad. Sc., 1998, pp. 10884-10889, vol. 95.

Lindholm, D., et al., "Glucocorticoid Hormones Negatively Regulate Nerve Growth Factor Expression In Vivo and in Cultured Rat Fibroblasts", Eur. J. Neurosci., 1990, pp. 795-801, vol. 2.

Lindsay, R.M., "Nerve Growth Factors (NGF, BDNF) Enhance Axonal Regeneration But Are Not Required for Survival of Adult Sensory Neurons", J. Neurosci., 1988, pp. 2394-2405, 8(7).

Lindsay, R.M., et al., "Nerve Growth Factor Regulates Expression of Neuropeptide Genes in Adult Sensory Neurons", Nature, 1989, pp. 362-364, vol. 337.

Liu, Z.Z., et al., "Critical Role of TrkB and Brain-Derived Neurotrophic Factor in the Differentiation and Survival of Retinal Pigment Epithelium", J. Neurosci., 1997, pp. 8749-8755, 17(22).

Lobuglio, A.F., et al., "Mouse/Human Chimeric Monoclonal Antibody in Man: Kinetics and Immune Response", Proc. Natl. Acad. Sci., 1989, pp. 4220-4224, vol. 86.

Lonberg, N., et al., "Human Antibodies From Transgenic Mice", Int. Rev. Immunol., 1995, pp. 65-93, vol. 13.

Mahato, R.I., et al., "Cationic Lipid-Based Gene Delivery Systems: Pharmaceutical Perspectives", Pharm. Res., 1997, pp. 853-859, 14(7).

Manni, L., et al., "Role of IL-1β and TNF-α in the Regulation of NGF in Experimentally Induced Arthritis in Mice", Rheumatol., 1998, pp. 97-102, vol. 18.

Marks, J.D., et al., "By-Passing Immunization: Human Antibodies From V-Gene Libraries Displayed on Phage", J. Mol. Biol., 1991, pp. 581-597, vol. 222.

Marks, J.D., et al., "By-Passing Immunization: Building High Affinity Human Antibodies by Chain Shuffling", Bio/Technol., 1992, pp. 779-783, vol. 10.

Matsuda, H., et al., "Nerve Growth Factor Promotes Human Hemopoietic Colony Growth and Differentiation", Proc. Natl. Acad. Sci., 1988, pp. 6508-6512, vol. 85.

Matsuda, H., et al., "Role of Nerve Growth Factor in Cutaneous Wound Healing: Accelerating Effects in Normal and Healing-Impaired Diabetic Mice", J. Exp. Med., 1998, pp. 297-330, 187(3).

McCafferty, J., et al., "Phage Antibodies, Filamentous Phage Displaying Antibody Variable Domains", Nature, 1990, pp. 552-553, vol. 348.

Meenan, R.F., et al., "The Arthritis Impact Measurement Scales", Arthritis and Rheumatism, 1982, pp. 1048-1053, 25(9).

Michael, G.J., et al., "Nerve Growth Factor Treatment Increases Brain-Derived Neurotrophic Factor Selectively in TrkA-Expressing Dorsal Root Ganglion Cells and in Their Central Terminations Within the Spinal Cord", J. Neurosci., 1997, pp. 8476-8490, 17(21).

Miletic, G., et al., "Increases in the Concentration of Brain Derived Neurotrophic Factor in the Lumbar Spinal Dorsal Horn are Associated with Pain Behavior Following Chronic Constriction Injury in Rats", Neurosci. Lett., 2002, pp. 137-140, vol. 319.

Milstein, C., et al., "Hybrid Hydridomas and Their Use in Immunohistochemistry", Nature, 1983, pp. 537-539, vol. 305.

Møiniche, S., et al., "Time Course of Subjective Pain Ratings, and Wound and Leg Tenderness After Hysterectomy", Acta Anaesthesiol. Scand., 1997, pp. 785-789, vol. 41.

Møiniche, S., et al., "A Qualitative and Quantitative Systematic Review of Preemptive Analgesia for Postoperative Pain Relief", Anesthesiology, 2002, pp. 725-741, vol. 96.

Morrison, S.L., et al., "Chimeric Human Antibody Molecules: Mouse Antigen-Binding Domains with Human Constant Region Domains", Proc. Natl. Acad. Sci., 1984, pp. 6851-6855, vol. 81.

Myers, E.W., et al., "Optimal Alignments in Linear Space", CABIOS, 1988, pp. 11-17, 4(1).

Okragly, A.J., et al., "Elevated Tryptase, Nerve Growth Factor, Neurotrophin-3 and Glial Cell Line-Derived Neurotrophic Factor Levels in the Urine of Interstitial Cystitis and Bladder Cancer Patients", J. Urology, 1991, pp. 438-442, vol. 161.

Otten, U., et al., "Nerve Growth Factor Induces Plasma Extravasation in Rat Skin", Eur. J. Pharmacol., 1984, pp. 199-201, vol. 106.

Otten, U., et al., "Nerve Growth Factor Induces Growth and Differentiation of Human B Lymphocytes", Proc. Natl. Acad. Sci., 1989, pp. 10059-10063, vol. 86.

Paulus, H.E., et al., "Analysis of Improvement in Individual Rheumatoid Arthritis Patients Treated with Disease-Modifying Antirheumatic Drugs, Based on the Findings in Patients Treated with Placebo", Arthritis and Rheumatism, 1990, pp. 477-484, 33(4).

Pearce, F.L., et al., "Some Characteristics of Histamine Secretion From Rat Peritoneal Mast Cells Stimulated with Nerve Growth Factor", J. Physiol., 1986, pp. 379-393, vol. 372.

Pearson, C.M., et al., "Studies of Polyarthritis and Other Lesions Induced in Rats by Injection of Mycobacterial Adjuvant. I. General Clinical and Pathologic Characteristics and Some Modifying Factors", Arthritis Rheum., 1959, pp. 440-459, vol. 2.

Peeters, K., et al., "Production of Antibodies and Antibody Fragments in Plants", Vaccine, 2001, pp. 2756-2761, vol. 19.

Petersen, M., et al., "Nerve Growth Factor Regulates the Expression of Bradykinin Binding Sites on Adult Sensory Neurons Via the Neurotrophin Receptor p75", Neuroscience, 1998, pp. 161-168, 83(1).

Petty, B.G., et al., "The Effect of Systemically Administered Recombinant Human Nerve Growth Factor in Healthy Human Subjects", Annals Neurol., 1994, pp. 244-246, vol. 36.

Philip, R., et al., "Efficient and Sustained Gene Expression in Primary T Lymphocytes and Primary and Cultured Tumor Cells Mediated by Adeno-Associated Virus Plasmid DNA Complexed to Cationic Liposomes", Mol. Cell Biol., 1994, pp. 2411-2418, 14(4).

Pogatzki, E.M., et al., "Characterization of Aδ- and C-Fibers Innervating the Plantar Rat Hindpaw One Day After an Incision", J. Neurophysiol. 2002, pp. 721-731, vol. 87.

Pogatzki, E.M., et al., "Role of Rostral Medial Medulla in the Development of Primary and Secondary Hyperalgesia After Incision in the Rat", Anesthesiology, 2002, pp. 1153-1160, vol. 96.

Poljak, R.J., et al., "Production and Structure of Diabodies", Structure, 1994, pp. 1121-1123, vol. 2.

Pollock, D.P., et al., "Transgenic Milk as a Method for the Production of Recombinant Antibodies", J. Immunol. Methods, 1999, pp. 147-157, vol. 231.

Pons, J., et al., "Energetic Analysis of an Antigen/Antibody Interface: Alanine Scanning Mutagenesis and Double Mutant Cycles on the HyHEL-10/Lysozyme Interaction", Prot. Sci., 1999, pp. 958-968, vol. 8.

Prodromou, C., et al., "Recursive PCR: A Novel Technique for Total Gene Synthesis", Protein Eng., 1992, pp. 827-829, 5(8).

Ravetch, J.V., et al., "Fc Receptors", Ann. Rev. Immunol., 1991, pp. 457-492, vol. 9.

Raychaudhuri, S.P., et al., "Psoriatic Keratinocytes Express High Levels of Nerve Growth Factor", Acta Derm Venereol., 1998, pp. 84-86, vol. 78.

Riechmann, L., et al., "Reshaping Human Antibodies for Therapy", Nature, 1988, pp. 323-327, vol. 332.

Ro, L-S., et al., "Effect of NGF and Anti-NGF on Neuropathic Pain in Rats Following Chronic Constriction Injury of the Sciatic Nerve", Pain, 1999, pp. 265-274, vol. 79.

Robinson, D.F., "Comparison of Labeled Trees with Valency Three", J. Comb. Theor., 1971, pp. 105-119, vol. 11.

Rossi, J.J., et al., eds. (1999) "Intracellular Ribozyme Applications: Principles and Protocols", Horizon Scientific Press: Duarte, CA pp. iii-iv (Table of Contents Only).

Roubenoff, R., et al., "Rheumatoid Cachexia: Cytokine-Drive Hypermetabolism Accompanying Reduced Body Cell Mass in Chronic Inflammation", J. Clin. Invest., 1994, pp. 2379-2386, 93(6).

Roubenoff, R., et al., "Adjuvant Arthritis as a Model of Inflammatory Cachexia", Arthritis Rheum.,1997, pp. 534-539, 40(3).

Ruberti, F., et al., "Cloning and Expression of an Anti-Nerve Growth Factor (NGF) Antibody for Studies Using the Neuroantibody Approach", Cell. Molec. Neurobiol., 1993, pp. 559-568, 13(5).

Saitou, N., et al., "The Neighbor-Joining Method: A New Method for Reconstructing Phylogenetic Tree", Mol. Biol. Evol., 1987, pp. 406-425, 4(4).

Schwartz, F., et al., "Effect of Helium/Neon Laser Irradiation on Nerve Growth Factor Synthesis and Secretion in Skeletal Muscle Cultures", J. Photochem. Photobiol. B. Biology, 2002, pp. 195-200, vol. 66.

Sevarino, K.A., et al., "Biosynthesis of Thyrotropin-Releasing Hormone by a Rat Medullary Thyroid Carcinoma Cell Line", J. Biol. Chem., 1988, pp. 620-623, vol. 263.

Shaw, D.R., et al., "Characterization of a Mouse/Human Chimeric Monoclonal Antibody (17-1A) To A Colon Cancer Tumor-Associated Antigen", J. Immunol., 1987, pp. 4534-4538, 138(12).

Sheets, M.D., et al., "Efficient Construction of a Large Nonimmune Phage Antibody Library: The Production of High-Affinity Human Single-Chain Antibodies to Protein Antigens", Proc. Natl. Acad. Sci., 1998, pp. 6157-6162, vol. 95.

Smyene, R.J., et al., "Severe Sensory and Sympathetic Neuropathies in Mice Carrying a Disrupted Trk/NGF Receptor Gene", Nature, 1994, pp. 246-249, vol. 368.

Sneath, P.H.A., et al., (1973). Numerical Taxonomy the Principles and Practice of Numerical Taxonomy, W.H. Freeman Press: San Francisco, CA. pp. vii-ix (Table of Contents Only).

Steiner, P., et al., "Interleukin-1β and Tumor Necrosis Factor-a Synergistically Stimulate Nerve Growth Factor Synthesis in Rat Mesangial Cells", Am. J. Physiol., 1991, pp. F792-F798, vol. 261.

Taglialatela, G., et al., "Suppression of p140$^{trkA}$ Does Not Abolish Nerve Growth Factor-Mediated Rescue of Serum-Free PC12 Cells", J. Neurochem., 1996, pp. 1826-1835, 66(5).

Thompson, S.W.N., et al., "Nerve Growth Factor Induces Mechanical Allodynia Associated with Novel A Fibre-Evoked Spinal Reflex Activity and Enhanced Neurokinin-1 Receptor Activation in the Rat", Pain, 1995, pp. 219-231, vol. 62.

Thompson, S.W.N., et al., "Brain-Derived Neurotrophic Factor is an Endogenous Modulator of Nociceptive Responses in the Spinal Cord", Proc. Natl. Acad. Sci., 1999, pp. 7714-7718, 96(14).

Torcia, M., et al., "Nerve Growth Factor Is an Autocrine Survival Factor for Memory B Lymphocytes", Cell, 1996, pp. 345-356.

Tsoulfas, P., et al., "The Rat trkC Locus Encodes Multiple Neurogenic Receptors That Exhibit Differential Response to Neurotrophin-3 in PC12 Cells", Neuron., 1993, pp. 975-990, vol. 10.

Ueyama, T., et al., "Production of Nerve Growth Factor by Cultured Vascular Smooth Muscle Cells From Spontaneously Hypertensive and Wistar-Kyoto Rats", J. Hypertens., 1993, pp. 1061-1065, vol. 11.

Ullrich, A., et al., "Human β-Nerve Growth Factor Gene Sequence Highly Homologous to That of Mouse", Nature, 1983, pp. 821-825, vol. 303.

Umana, P., et al., "Engineered Glycoforms of an Antineuroblastoma IgG1 with Optimized Antibody-Dependent Cellular Cytotoxic Activity", Mature Biotech., 1999, pp. 176-180, vol. 17.

Urfer, R., et al., "Specificity Determinants in Neurotrophin-3 and Design of Nerve Growth Factor-Based trkC Agonists by Changing Central β-Strand Bundle Residues to Their Neurtrophin-3 Analogs", Biochem., 1997, pp. 4775-4781, vol. 36.

Valenzuela, D.M., et al., "Alternative Forms of Rat TrkC With Different Functional Capabilities", Neuron., 1993, pp. 963-974, vol. 10.

Vaughan, T.J., et al., "Human Antibodies with Sub-Nanomolar Affinities Isolated from a Large Non-Immunized Phage Display Library", Nature Biotechnology, 1996, pp. 309-314, vol. 14.

Verhoeyen, M., et al., "Reshaping Human Antibodies: Grafting an Antilysozyme Activity", Science, 1988, pp. 1534-1536, vol. 239.

Waterhouse, P., et al., "Combinatorial Infection and in vivo Recombination: A Strategy for Making Large Phage Antibody Repertoires", Nucl. Acids Res., 1993, pp. 2265-2266, 21(9).

Wilbur, W.J., et al., "Rapid Similarity Searches of Nucleic Acid and Protein Data Banks", Proc. Natl. Acad. Sci., 1983, pp. 726-730, vol. 80.

Winter, G., et al., "Man-Made Antibodies", Nature, 1991, pp. 293-299, vol. 349.

Winter, G., et al., "Making Antibodies by Phage Display Technology", Annu. Rev. Immunol., 1994, pp. 433-455, vol. 12.

Wittwer, A.J., et al., "Glycosylation at Asn-184 Inhibits the Conversion of Single-Chain to Two-Chain Tissue-Type Plasminogen Activator by Plasmin", Biochem.,1990, pp. 4175-4180, vol. 29.

Woffendin, C., et al., "Nonviral and Viral Delivery of a Human Immunodeficiency Virus Protective Gene into Primary Human T Cells", Proc. Natl. Acad. Sci., 1994, pp. 11581-11585, vol. 91.

Woolf, C.J., et al., "Peripheral Cell Types Contributing to the Hyperalgesic Action of Nerve Growth Factor in Inflammation", J. Neurosci., 1996, pp. 2716-2723, 16(8).

Woolf, N. J., et al., "Elevation of Nerve Growth Factor and Antisense Knockdown of TrkA Receptor during Contextual Memory Consolidation", J. Neurosci., 2001, pp. 1047-1055, 21(3).

Wright, A., et al., "Effect of Glycosylation on Antibody Function: Implications for Genetic Engineering", *TibTECH*, 1997, pp. 26-32, vol. 15.

Wu, C.H., et al., "Targeting Genes: Delivery and Persistent Expression of a Foreign Gene Driven by Mammalian Regulatory Elements in Vivo", J. Biol. Chem., 1989, pp. 16985-16987, vol. 264.

Wu, G.Y., et al., "Receptor-Mediated Gene Delivery in Vivo: Partial Correction of Genetic Analbuminemia in Nagase Rats", J. Biol. Chem., 1991, pp. 14338-14342, 266(22).

Wu, G.Y., et al., "Incorporation of Adenovirus into a Ligand-Based DNA Carrier System Results in Retention of Original Receptor Specificity and Enhances Targeted Gene Expression", J. Biol. Chem., 1994, pp. 11542-11546, 269(15).

Wyss, D.F., et al., "The Structural Role of Sugars in Glycoproteins", Current Opin. Biotech., 1996, pp. 409-416, vol. 7.

Yamamoto, T., et al., "Spinal $N$-acetyl-α-linked Acidic Dipeptidase (NAALADase) Inhibition Attenuates Mechanical Allodynia Induced by Paw Carrageenan Injection in the Rat", Brain Res., 2001, pp. 138-144, vol. 909.

Yan, Q, et al., "Hypotension Induced by Intravascular Administration of Nerve Growth Factor in the Rat", Clin. Sci., 1991, pp. 565-569, vol. 80.

Zenke, M., et al., "Receptor-Mediated Endocytosis of Transferrin-Polycation Conjugates: An Efficient Way to Introduce DNA Into Hematopoietic Cells", Proc. Natl. Acad. Sci., 1990, pp. 3655-3659, vol. 87.

Zola, H., "Using Monoclonal Antibodies: Soluble Antigens", *In* Monocolonal Antibodies: A Manual of Techniques, CRC Press, Inc., Chapter 6, pp. 147-158, 1987.

* cited by examiner

SEQUENCE LISTING

```
<160> NUMBER OF SEQ ID NOS: 8

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser
        115                 120

<210> SEQ ID NO 2
<211> LENGTH: 109
```

```
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Glu His Thr Leu Leu Pro Tyr
                85                  90                  95

Thr Phe Gly Gln Gly Thr Lys Leu Glu Ile Lys Arg Thr
            100                 105

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Phe Ser Leu Ile Gly Tyr Asp Leu Asn
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Ile Ile Trp Gly Asp Gly Thr Thr Asp Tyr Asn Ser Ala Val Lys Ser
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Gly Gly Tyr Trp Tyr Ala Thr Ser Tyr Tyr Phe Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Arg Ala Ser Gln Ser Ile Ser Asn Asn Leu Asn
1               5                   10
```

```
<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Tyr Thr Ser Arg Phe His Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gln Gln Glu His Thr Leu Pro Tyr Thr
1               5
```

METHODS FOR TREATING PAIN BY ADMINISTERING A NERVE GROWTH FACTOR ANTAGONIST AND AN NSAID AND COMPOSITIONS CONTAINING THE SAME

CROSS-REFERENCE TO RELATED APPLICATIONS

This application is a continuation of application US. Ser. No. 10/783,730, filed Feb. 19, 2004, now allowed, which claims the priority benefit of provisional application U.S. Ser. Nos. 60/448,823, filed Feb. 19, 2003, and 60/448,853, filed Feb. 19, 2003, the contents of which are incorporated by reference in their entirety.

FIELD OF THE INVENTION

This invention relates to methods and compositions for preventing or treating pain in a patient by administering a combination of a nerve growth factor antagonist and an NSAID.

BACKGROUND OF THE INVENTION

A number of treatments involving the administration of non-steroidal anti-inflammatory drugs (NSAIDs) are currently recommended for pain relief. The administration of NSAIDs has been shown to display pain alleviating properties. However, treatment with NSAIDs has known disadvantages, including unwanted side effects such as irritation of the gastrointestinal tract and kidney and liver toxicity. Moreover, NSAIDs cannot achieve adequate pain alleviation even at their maximum therapeutically approved doses in some pain states.

Nerve growth factor (NGF) was the first neurotrophin identified, and its role in the development and survival of both peripheral and central neurons has been well characterized. NGF has been shown to be a critical survival and maintenance factor in the development of peripheral sympathetic and embryonic sensory neurons and of basal forebrain cholinergic neurons (Smeyne, et al., *Nature* 368:246-249 (1994); Crowley, et al., *Cell* 76:1001-1011 (1994)). NGF upregulates expression of neuropeptides in sensory neurons (Lindsay, et al., *Nature* 337:362-364 (1989)) and its activity is mediated through two different membrane-bound receptors, the TrkA tyrosine kinase receptor and the p75 receptor, which is structurally related to other members of the tumor necrosis factor receptor family (Chao, et al., *Science* 232:518-521 (1986)).

In addition to its effects in the nervous system, NGF has been increasingly implicated in processes outside of the nervous system. For example, exogenously administered NGF has been shown to enhance vascular permeability (Often, et al., *Eur. J. Pharmacol.* 106:199-201 (1984)), enhance T- and B-cell immune responses (Often, et al., *Proc. Natl. Acad. Sci. U.S.A.* 86:10059-10063 (1989)), induce lymphocyte differentiation and mast cell proliferation and cause the release of soluble biological signals from mast cells (Matsuda, et al., *Proc. Natl. Acad. Sci. U.S.A.* 85:6508-6512 (1988); Pearce, et al., *J. Physiol.* 372:379-393 (1986); Bischoff, et al., *Blood* 79:2662-2669 (1992); Horigome, et al., *J. Biol. Chem.* 268: 14881-14887 (1993)).

NGF is produced by a number of cell types including mast cells (Leon, et al., *Proc. Natl. Acad. Sci. U.S.A.* 91:3739-3743 (1994)), B-lymphocytes (Torcia, et al., *Cell* 85:345-356 (1996), keratinocytes (Di Marco, et al., *J. Biol. Chem.* 268: 22838-22846)), smooth muscle cells (Ueyama, et al., *J. Hypertens.* 11:1061-1065 (1993)), fibroblasts (Lindholm, et al., *Eur. J. Neurosci.* 2:795-801 (1990)), bronchial epithelial cells (Kassel, et al., *Clin, Exp. Allergy* 31:1432-40 (2001)), renal mesangial cells (Steiner, et al., *Am. J. Physiol.* 261: F792-798 (1991)) and skeletal muscle myotubes (Schwartz, et al., *J Photochem. Photobiol. B* 66:195-200 (2002)). NGF receptors have been found on a variety of cell types outside of the nervous system. For example, TrkA has been found on human monocytes, T- and B-lymphocytes and mast cells.

An association between increased NGF levels and a variety of inflammatory conditions has been observed in human patients as well as in several animal models. These include systemic lupus erythematosus (Bracci-Laudiero, et al., *Neuroreport* 4:563-565 (1993)), multiple sclerosis (Bracci-Laudiero, et al., *Neurosci. Lett.* 147:9-12 (1992)), psoriasis (Raychaudhuri, et al., *Acta Derm. l'enereol.* 78:84-86 (1998)), arthritis (Falcimi, et al., *Ann. Rheum. Dis.* 55:745-748 (1996)), interstitial cystitis (Okragly, et al., *J. Urology* 161:438-441 (1999)) and asthma (Braun, et al., *Eur. J Immunol.* 28:3240-3251 (1998)).

Consistently, an elevated level of NGF in peripheral tissues is associated with hyperalgesia and inflammation and has been observed in a number of forms of arthritis. The synovium of patients affected by rheumatoid arthritis expresses high levels of NGF while in non-inflamed synovium NGF has been reported to be undetectable (Aloe, et al., *Arch. Rheum.* 35:351-355 (1992)). Similar results were seen in rats with experimentally induced rheumatoid arthritis (Aloe, et al., *Clin. Exp. Rheumatol.* 10:203-204 (1992)). Elevated levels of NGF have been reported in transgenic arthritic mice along with an increase in the number of mast cells. (Aloe, et al., *Int. J. Tissue Reactions-Exp. Clin. Aspects* 15:139-143 (1993)).

There are two general categories of medication for the treatment of pain, each acting via different mechanisms and having differing effects, and both having disadvantages. The first category includes the nonsteroidal anti-inflammatory drugs (NSAIDs) which are used to treat mild pain, but whose therapeutic use is limited by undesirable gastrointestinal effects such as gastric erosion, formation of peptic ulcer or inflammation of the duodenum and of the colon and renal toxicity with prolonged use. The second category includes the opioid analgesics, such as morphine, which are used to treat moderate to severe pain but whose therapeutic use is limited because of undesirable effects such as constipation, nausea and vomiting, respiratory depression, mental clouding, renal colic, tolerance to prolonged use and risk of addiction.

It is evident that there is a need for an improved pain treatment that provides an improved therapeutic benefit (e.g., reduced severity and/or frequency of pain) and/or reduces the incidence of unwanted side effects caused by many of the current regimens.

All references cited herein, including patent applications and publications, are incorporated by reference in their entirety.

Deposit Information

Applicants have deposited the polynucleotides encoding the E3 heavy chain and the E3 light chain variable region of the antibody designated as E3 herein with the American Type Culture Collection (ATCC) Manassas, Va. 20110-2209 U.S.A. As noted in the foregoing, the E3 antibody light chain variable region was deposited on Jan. 8, 2003 and was assigned ATCC Deposit No, PTA4893 (Vector Eb.911.3E) and ATCC Deposit No. PTA-4894 (Vector Eb.pur.911.3E), and the E3 antibody heavy chain variable region was deposited on Jan. 8, 2003 and was assigned ATCC Deposit No. PTA-4895 (Vector Db.911.3E). These deposits were made under the provisions of the Budapest Treaty on the International Recognition of the Deposit of Microorganisms for the Purpose of Patent Procedure and the Regulations thereunder (Budapest Treaty). These deposits will be maintained in the ATCC depository for a term of at least thirty (30) years and at least five (5) years after the most recent request for the furnishing of a sample of the deposited material or for the effective life of the patent, whichever is longer and will be replaced if the deposits become non-viable during that period.

Applicants have deposited the polynucleotides encoding the E3 heavy chain and the E3 light chain variable region of the antibody designated as E3 herein with the American Type Culture Collection (ATCC) Manassas, Va. 20110-2209 U.S.A. As noted in the foregoing, the E3 antibody light chain variable region was deposited on Jan. 8, 2003 and was assigned ATCC Deposit No. PTA-4893 (Vector Eb.911.3E) and ATCC Deposit No. PTA-4894 (Vector Eb.pur.911.3E), and the E3 antibody heavy chain variable region was deposited on Jan. 8, 2003 and was assigned ATCC Deposit No. PTA-4895 (Vector Db.911.3E). These deposits were made under the provisions of the Budapest Treaty on the International Recognition of the Deposit of Microorganisms for the Purpose of Patent Procedure and the Regulations thereunder (Budapest Treaty). These deposits will be maintained in the ATCC depository for a term of at least thirty (30) years and at least five (5) years after the most recent request for furnishing of a sample of the deposited material or for the effective life of the patent, whichever is longer, and will be replaced if the deposits become non-viable during that period.

BRIEF SUMMARY OF THE INVENTION

The present invention is based upon the discovery that antagonists of NGF are effective in treating pain in conjunction with an NSAID. Such therapy results in unexpectedly enhanced pain treatment. In addition, such therapy generally allows a reduced dosage of NSAID to effect the same amount of pain reduction and/or other forms of enhancement of NSAID pain treatment.

In a first aspect, the present invention features a method for treating (or, in other embodiments, preventing) pain comprising administering an amount of a nerve growth factor antagonist and an amount of an NSAID such that in conjunction they provide effective pain relief The relative amounts and ratios of NGF antagonist and NSAID may vary. In some embodiments, enough NGF antagonist will be administered so as to allow reduction of the normal dose of NSAID required to effect the same degree of pain amelioration. In some embodiments, enough NGF antagonist will be administered so as to allow reduction of the normal dose of NSAID required to effect the same degree of pain amelioration by at least about 5%, at least about 10%, at least about 20%, at least about 30%, at least about 40%, at least about 50%, at least about 60%, at least about 70%, at least about 80%, or at least about 90%, or more. This reduction may be reflected in terms of amount administered at a given administration and/or amount administered over a given period of time (reduced frequency).

In another aspect, the invention provides methods for enhancing NSAID pain treatment comprising administering an effective amount of an NSAID in conjunction with an effective amount of an NGF antagonist. Administration in conjunction, as used herein, comprises simultaneous administration and/or administration at different times. Administration in conjunction also encompasses administration as a co-formulation (i.e., the NGF antagonist and NSAID are present (combined) in the same composition) and/or administration as separate compositions. As used herein, "administration in conjunction" is meant to encompass any circumstance wherein an NSAID and NGF antagonist are administered in an effective amount to an individual. As further discussed herein, it is understood that the NGF antagonist and NSAID can be administered at different dosing frequencies and/or intervals. For example, an anti-NGF antibody can be administered weekly, while an NSAID can be administered more frequently. It is understood that the NGF antagonist and the NSAID can be administered using the same route of administration or different routes of administration, and that different dosing regimens may change over the course of administration(s). Administration may be before the onset of pain.

In another aspect, the invention provides methods for reducing incidence of pain, ameliorating pain, palliating pain, and/or delaying the development or progression of pain in an individual, said methods comprising administering an effective amount of an NGF antagonist in conjunction with an effective amount of an NSAID.

The methods of the invention are suitable for treating or preventing any pain of any etiology, including pain where the use of an NSAID is generally prescribed. In some embodiments, the pain is post-surgical pain. In some embodiments, the pain is pain associated with burn. In other embodiments, the pain is pain associated with rheumatoid arthritis. In other embodiments, the pain is pain associated with osteoarthritis.

An NGF antagonist suitable for use in the methods of the invention is any agent that can directly or indirectly result in decreased NGF biological activity. In some embodiments, an NGF antagonist binds (physically interacts with) NGF (e.g., an antibody), binds to an NGF receptor (such as trkA receptor and/or p75) and/or reduces (impedes and/or blocks) downstream NGF receptor signaling (e.g., inhibitors of kinase signaling or other downstream signaling induced by NGF in a target cell). In other embodiments, an NGF antagonist inhibits (reduces) NGF synthesis and/or release. In other embodiments, an NGF antagonist decreases the expression or function of an NGF receptor TrkA and/or p75. In another embodiment, the NGF antagonist is an NGF antagonist that is not a TrkA immunoadhesin (i.e., is other than a TrkA immunoadhesin). In some embodiments, the NGF antagonist is selected from any one or more of the following: an anti-NGF antibody, an anti-sense molecule directed to a nucleic acid encoding an NGF (including an anti-sense molecule directed to a nucleic acid encoding NGF), an anti-sense molecule directed to an NGF receptor (such as TrkA and/or p75), an NGF inhibitory compound, an NGF structural analog, a dominant-negative mutation of a TrkA and/or p75 receptor that binds an NGF, an anti-TrkA antibody, an anti-p75 antibody and a kinase inhibitor. In some embodiments, the NGF antagonist (such as anti-NGF antibody) binds NGF (such as hNGF) and does not significantly bind to related neurotrophins, such as NT-3, NT4/5, and/or BDNF. In another embodiment, the NGF antagonist is an anti-NGF antibody. In still other embodiments, the anti-NGF antibody binds specifically to NGF. In still other embodiments, the anti-NGF antibody recognizes human NGF. In yet other embodiments, the anti-NGF antibody specifically binds human NGF. In still further embodiments, the antibody binds essentially the same NGF epitope 6 as an antibody selected from any one or more of the following: MAb 911, MAb 912 and MAb 938 (See Hongo, et al., *Hybridoma* 19:215-227 (2000)). In still other embodiments, the anti-NGF antibody is humanized (including humanized Mab 911, such as antibody E3 described herein). In still other embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the anti-NGF antibody is human. In still other embodiments, the anti-NGF antibody comprises the amino acid sequence of the heavy chain variable region shown in Table 1 (SEQ ID NO:1) and the amino acid sequence of the light chain variable region shown in Table 2 (SEQ ID NO:2). In still other embodiments, the anti-NGF antibody comprises the amino acid sequence of the heavy chain variable region shown in Table 1 (SEQ ID NO:1). In still other embodiments, the anti-NGF antibody comprises the amino acid sequence of the light chain variable region shown in Table 2 (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT Application No. PCT/GB99/01441; and/or UK Patent Application No. 9809951.8.

In some embodiments, the NGF antagonist binds to the NGF molecule. In still other embodiments, the NGF antagonist is an antibody that binds specifically to NGF. However, the NGF antagonist may alternatively bind to the trkA receptor. The NGF antagonist may be an anti-human NGF (anti-hNGF) monoclonal antibody that is capable of binding hNGF and effectively inhibiting the binding of hNGF to human TrkA (hTrkA).

The binding affinity of an anti-NGF antibody to NGF (such as hNGF) can be about 0.10 nM to about 0.80 nM, about 0.15 to about 0.75 nM and about 0.18 to about 0.72 nM. In one embodiment, the binding affinity is between about 2 pM and 22 pM. In some embodiments, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM, or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, about 40 pM, or about 50 pM. In some embodiments, the binding affinity is any of about 100 nM, about 50 nM, about 10 nM, about 1 nM, about 500 pM, about 100 pM, or about 50 pM, or less than about 50 pM. In some embodiments, the binding affinity is less than any of about 100 nM, about 50 nM, about 10 nM, about 1 nM, about 500 pM, about 100 pM, or about 50 pM. In still other embodiments, the binding affinity is about 2 pM, about 5 pM, about 10 pM, about 15 pM, about 20 pM, about 40 pM, or greater than about 40 pM. As is well known in the art, binding affinity can be expressed as $K_D$, or dissociation constant, and an increased binding affinity corresponds to a decreased $K_D$. The binding affinity of anti-NGF mouse monoclonal antibody 911 (Hongo et al., Hybridoma 19:215-227 (2000)) to human NGF is about 10 nM, and the binding affinity of humanized anti-NGF antibody E3 (described herein) to human NGF is about 0.07 nM.

In instances where the NGF antagonist is an antibody, the antibody may be an antibody fragment, including an antibody fragment selected from the group consisting of Fab, Fab', F(ab')2, Fv fragments, diabodies, single chain antibody molecules and multispecific antibodies formed from antibody fragments, and a single-chain Fv (scFv) molecule.

The NSAID may be any non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam.

Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), rofecoxib, DUP-697, flosulide (CGP-28238), meloxicam, 6-methoxy-2 naphthylacetic acid (6-MNA), MK-966, nabumetone (prodrug for 6-MNA), nimesulide, NS-398, SC-5766, SC-58215, T-614; or combinations thereof.

In some embodiments, the invention provides methods in which aspirin and/or acetaminophen are used in conjunction with NGF antagonist (such as anti-NGF antibody).

The NGF antagonist and/or NSAID can be administered to an individual via any suitable route. For example, they can be administered together or separately, and/or simultaneously and/or sequentially, orally, intravenously, sublingually, subcutaneously, intraarterially, intramuscularly, rectally, intraspinally, intrathoracically, intraperitoneally, intraventricularly, sublingually, transdermally or by inhalation. Administration can be systemic, e.g., intravenous, or localized.

In a second aspect, the present invention features compositions comprising a nerve growth factor antagonist and an NSAID. The nerve growth factor antagonist and the NSAID may be present together with one or more pharmaceutically acceptable carriers or excipients, or they may be present in separate compositions. In another aspect, the invention provides a synergistic composition of an NGF antagonist and an NSAID.

In a third aspect, the present invention features a kit for use in any of the methods disclosed herein, said kit comprising an NGF antagonist and an NSAID. The kit may further comprise instructions for any of the methods described herein. The instructions may comprise administration of NGF antagonist (such as anti-NGF antibody) in conjunction with NSAID (i.e., simultaneous administration and/or administration at different times). In some embodiments, the NGF antagonist and NSAID are packaged together, but they may or may not be in the same container. Thus, in some embodiments, the kit comprises an NGF antagonist and an NSAID present in the same container, and instructions for use in any of the methods described herein. In other embodiments, the kit comprises an NGF antagonist and an NSAID present in separate containers.

In some embodiments, the invention provides a method for treating pain in an individual comprising administering to the individual an effective amount of an anti-nerve growth factor (NGF) antibody and an NSAID. In some embodiments, the NSAID is selected from the group consisting of ibuprofen, naproxen, naprosyn, diclofenac, ketoprofen, tolmetin, slindac, mefenamic acid, meclofenamic acid, diflunisal, flufenisal, piroxim, sudoxicam, isoxicam, celecoxib, rofecoxib, DUP-697, flosulide, meloxicam, 6-methoxy-2 naphthylacetic acid, MK-966, nabumetone, nimesulide, NS-398, SC-5766, SC-58215, T-614. In some embodiments, the NSAID is ibuprofen. In some embodiments, the anti-NGF antibody binds human NGF. In some embodiments, the anti- NGF antibody binds human NGF with a binding affinity of about 10 nM or less than about 10 nM. In some embodiments, the anti-NGF antibody is a human antibody. In some embodiments, the anti-NGF antibody is a humanized antibody. In some embodiments, the humanized antibody is an antibody comprising the heavy chain variable region shown in SEQ ID NO:1 and the light chain variable region shown in SEQ ID NO:2. In some embodiments, the pain is post-surgical pain.

In some embodiments, the invention provides a pharmaceutical composition for treating pain comprising an effective amount of an anti-NGF antibody and an NSAID, and a pharmaceutically acceptable carrier.

In some embodiments, the invention provides a kit for treating pain comprising an anti-NGF antibody, an NSAID, and instructions for administering the anti-NGF antibody in conjunction with the NSAID to treat pain.

BRIEF DESCRIPTION OF THE DRAWING(S)

FIG. 1 demonstrates that the cumulative pain score is reduced in animals treated with S[+] ibuprofen at 10 or 30 mg/kg, in combination with an NGF antagonist (anti-NGF antagonist Mab 911; see Hongo et al, *Hybridoma* 19:215-227 (2000)). Animals were divided into two groups (control and antibody-treated). NGF antagonist was given 15 hours before surgery, intraperitoneal (time=−15 hours) at a dose of 1 mg/kg. Surgery was performed as described at time 0. Resting pain was assessed 24 hours after surgery ("0" in the graph). All animals were then treated with ibuprofen (300 mg/ml in 45% beta-cyclodextrin liquid) at 10 mg/kg or 30 mg/kg body weight. Non-antibody treated control animals were also treated with ibuprofen at 10 mg/kg, 30 mg/kg, 100 mg/kg, and 300 mg/kg. Ibuprofen was delivered sub-cutaneously in the scruff. One hour after the dose of ibuprofen, resting pain was tested. Treatment with anti-NGF antagonist antibody plus ibuprofen is more effective in reducing resting pain than treatment with either ibuprofen alone or anti-NGF antagonist antibody alone.

FIG. 2 is a graph showing cumulative pain score in animals treated with diclofenac at 5 mg/kg, in combination with an NGF antagonist (anti-NGF antagonist Mab 911; see Hongo et al, *Hybridoma* 19:215-227 (2000)). Animals were divided into two groups (control and antibody-treated). NGF antagonist was given 15 hours before surgery, intraperitoneal (time=−15 hours) at a dose of 1 mg/kg. Surgery was performed as described at time 0. Resting pain was assessed 24 hours after surgery ("0" in the graph). All animals were then treated with diclofenac at 5 mg/kg body weight. Non-antibody treated control animals were also treated with diclofenac at 5 mg/kg. Diclofenac was delivered sub-cutaneously in the scruff. One hour after the dose of diclofenac, resting pain was tested.

DETAILED DESCRIPTION OF THE INVENTION

We have discovered that pain may be prevented or treated by administering an effective amount of an NGF antagonist (such as an anti-NGF antibody) in conjunction with an NSAID. The methods and compositions of the present invention are useful for the treatment or prevention of pain, including any pain where the use of an NSAID is generally prescribed. By the use of a nerve growth factor antagonist and an NSAID in conjunction, in accordance with the present invention, it is now possible to treat pain with a lower dose of an NSAID thereby reducing the likelihood of side-effects associated with NSAID treatment. In some embodiments, enough NGF antagonist will be administered so as to allow reduction of the normal dose of NSAID required to effect the same degree of pain amelioration by at least about 5%, at least about 10%, at least about 20%, at least about 30%, at least about 50%, at least about 60%, at least about 70%, or at least about 90%, or more.

The treatment of pain with an NSAID can also be enhanced as described herein, by administration of the NSAID in conjunction with an NGF antagonist.

In one aspect, the invention provides methods of treating or preventing pain in an individual (such as a mammal, both human and non-human) comprising administering an effective amount of an NGF antagonist in conjunction with an effective amount of an NSAID. In another aspect, the invention provides methods of enhancing NSAID treatment or prevention of pain in an individual comprising administering an effective amount of an NGF antagonist (such as an anti-NGF antibody) in conjunction with an effective amount of an NSAID. In another aspect, the invention provides methods of preventing, ameliorating and/or preventing the development or progression of pain.

In some embodiments, the anti-NGF antibody is capable of binding NGF and effectively inhibiting the binding of NGF to its TrkA or p75 receptor in vivo or effectively inhibiting NGF from activating its TrkA or p75 receptor. In some embodiments, the binding affinity of the antibody to NGF is about 0.01 to about 1.00 nM, or about 0.05 to about 0.25 nM. In other embodiments, the binding affinity is about 1 pM, about 2 pM, about 5 pM, about 10 pM, about 15 pM, about 20 pM, about 50 pM, about 100 pM, or more. In one embodiment, the binding affinity is between about 2 pM and 22 pM. In some embodiments, the antibody binds essentially the same NGF epitope 6 as an antibody selected from any one or more of the following: MAb 911, MAb 912 and MAb 938. See Hongo, et al., *Hybridoma* 19:215-227 (2000).

The antibody may also be an antibody fragment, such as an antibody fragment selected from one or more of the following: Fab, Fab', F(ab')2, Fv fragments, diabodies, single chain antibody molecules and multispecific antibodies formed from antibody fragments, and a single-chain Fv (scFv) molecule. The antibody may also be chimeric, and it may be humanized or human. The antibody may also be bispecific.

Exemplary NSAIDs useful in the present invention include, but are not limited to, (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), rofecoxib, DUP-697, flosulide (CGP-28238), meloxicam, 6-methoxy-2 naphthylacetic acid (6-MNA), MK-966, nabumetone (prodrug for 6-MNA), nimesulide, NS-398, SC-5766, SC-58215, T-614; or combinations thereof. In some embodiments, aspirin and/or acetominophen are used in conjunction with NGF antagonist (such as anti-NGF antibody).

The methods and compositions of the present invention are useful for the treatment of pain of any etiology, including acute and chronic pain, any pain with an inflammatory component, and any pain in which an NSAID is usually prescribed. Examples of pain include post-surgical pain, postoperative pain (including dental pain), migraine, headache and trigeminal neuralgia, pain associated with burn, wound or kidney stone, pain associated with trauma (including traumatic head injury), neuropathic pain, pain associated with musculo-skeletal disorders such as rheumatoid arthritis, osteoarthritis, visceral pain, colitis, pancreatitis, gastritis, ankylosing spondylitis, sero-negative (non-rheumatoid) arthropathies, non-articular rheumatism and peri-articular disorders, and pain associated with cancer (including "breakthrough pain" and pain associated with terminal cancer), peripheral neuropathy, post-herpetic neuralgia, and pain associated with sickle-cell crisis. Examples of pain with an inflammatory component (in addition to some of those described above) include rheumatic pain, pain associated with mucositis, and dysmenorrhea. In some embodiments, the methods and compositions of the present invention are used for treatment or prevention of post-surgical pain and/or cancer pain. In other embodiments, the pain is a pain indication for which an NSAID is not generally prescribed, such as neuropathic pain. In other embodiments, the methods and compositions described herein are used for treatment and/or prevention of pain associated with burn. In other embodiments, the methods and compositions described herein are used for treatment and/or prevention of pain associated with rheumatoid arthritis. In other embodiments, the methods and compositions described herein are used for treatment and/or prevention of pain associated with osteoarthritis.

In another aspect, the invention provides compositions and kits for treating pain comprising an NGF antagonist (such as an anti-NGF antibody) and an NSAID suitable for use in any of the methods described herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual,* second edition (Sambrook et al., 1989) Cold Spring Harbor Press; *Oligonucleotide Synthesis* (M. J. Gait, ed., 1984); *Methods in Molecular Biology,* Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction,* (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

Definitions

An "antibody" (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, humanized antibodies, chimeric antibodies, diabodies linear antibodies, single chain antibodies, multispecific antibodies (e.g., bispecific antibodies) and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody. In some instances, framework region (FR) residues or other residues of the human immunoglobulin replaced by corresponding non-human residues. Furthermore, humanized antibodies may comprise residues which are not found in the recipient antibody or in the donor antibody.

As used herein, the term "nerve growth factor" and "NGF" refers to nerve growth factor and variants (including, for example, splice variants and protein processing variants)

thereof that retain at least part of the activity of NGF. As used herein, NGF includes all mammalian species of native sequence NGF, including human, non-human primate, canine, feline, equine, or bovine.

"NGF receptor" refers to a polypeptide that is bound by or activated by NGF. NGF receptors include the TrkA receptor and the p75 receptor of any mammalian species, including, but are not limited to, human, canine, feline, equine, primate, or bovine.

An "NGF antagonist" refers to any molecule that blocks, suppresses or reduces (including significantly) NGF biological activity, including downstream pathways mediated by NGF signaling, such as receptor binding and/or elicitation of a cellular response to NGF. The term "antagonist" implies no specific mechanism of biological action whatsoever, and is deemed to expressly include and encompass all possible pharmacological, physiological, and biochemical interactions with NGF whether direct or indirect, or whether interacting with NGF, its receptor, or through another mechanism, and its consequences which can be achieved by a variety of different, and chemically divergent, compositions. Exemplary NGF antagonists include, but are not limited to, an anti-NGF antibody, an anti-sense molecule directed to an NGF (including an anti-sense molecule directed to a nucleic acid encoding NGF), an NGF inhibitory compound, an NGF structural analog, a dominant-negative mutation of a TrkA receptor that binds an NGF, a TrkA immunoadhesin, an anti-TrkA antibody, an anti-p75 antibody, an anti-sense molecule directed to either or both of the TrkA and/or p75 receptors (including anti-sense molecules directed to a nucleic aid molecule encoding TrkA or p75), and a kinase inhibitor. For purpose of the present invention, it will be explicitly understood that the term "antagonist" encompass all the previously identified terms, titles, and functional states and characteristics whereby the NGF itself, an NGF biological activity (including but not limited to its ability to mediate any aspect of pain), or the consequences of the biological activity, are substantially nullified, decreased, or neutralized in any meaningful degree. In some embodiments, an NGF antagonist binds (physically interact with) NGF (e.g., an antibody), binds to an NGF receptor (such as trkA receptor or p75 receptor), reduces (impedes and/or blocks) downstream NGF receptor signaling, and/or inhibits (reduces) NGF synthesis, production or release. In some embodiments, an NGF antagonist binds (physically interacts with) NGF (e.g., an antibody), binds to an NGF receptor (such as TrkA receptor or p75 receptor), and/or reduces (impedes and/or blocks) downstream NGF receptor signaling. In other embodiments, an NGF antagonist binds NGF and prevents TrkA receptor dimerization and/or TrkA autophosphorylation. In other embodiments, an NGF antagonist inhibits or reduces NGF synthesis and/or production (release). Examples of types of NGF antagonists are provided herein.

As used herein, an "anti-NGF antibody" refers to an antibody which is able to bind to NGF and inhibit NGF biological activity and/or downstream pathway(s) mediated by NGF signaling.

A "TrkA immunoadhesin" refers to a soluble chimeric molecule comprising a fragment of a TrkA receptor, for example, the extracellular domain of a TrkA receptor and an immunoglobulin sequence, which retains the binding specificity of the TrkA receptor.

"Biological activity" of NGF generally refers to the ability to bind NGF receptors and/or activate NGF receptor signaling pathways. Without limitation, a biological activity includes any one or more of the following: the ability to bind an NGF receptor (such as p75 and/or TrkA); the ability to promote TrkA receptor dimerization and/or autophosphorylation; the ability to activate an NGF receptor signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; and the ability to mediate pain.

The term "epitope" is used to refer to binding sites for (monoclonal or polyclonal) antibodies on antigens such as protein antigens.

As used herein, "treatment" is an approach for obtaining beneficial or desired clinical results. For purposes of this invention, beneficial or desired clinical results include, but are not limited to, one or more of the following: improvement or alleviation of any aspect of pain, including acute, chronic, inflammatory, neuropathic, or post-surgical pain. For purposes of this invention, beneficial or desired clinical results include, but are not limited to, one or more of the following: including lessening severity, alleviation of one or more symptoms associated with pain including any aspect of pain (such as shortening duration of pain, and/or reduction of pain sensitivity or sensation).

"Reducing incidence" of pain means any of reducing severity (which can include reducing need for and/or amount of (e.g., exposure to) other drugs and/or therapies generally used for this conditions), duration, and/or frequency (including, for example, delaying or increasing time to pain in an individual). As is understood by those skilled in the art, individuals may vary in terms of their response to treatment, and, as such, for example, a "method of reducing incidence of pain in an individual" reflects administering the NGF antagonist described herein in conjunction with an NSAID as described herein, based on a reasonable expectation that such administration may likely cause such a reduction in incidence in that particular individual.

"Ameliorating" pain or one or more symptoms of pain means a lessening or improvement of one or more symptoms of a pain as compared to not administering an NGF antagonist in conjunction with an NSAID. "Ameliorating" also includes shortening or reduction in duration of a symptom.

"Palliating" pain or one or more symptoms of pain means lessening the extent of one or more undesirable clinical manifestations of pain in an individual or population of individuals treated with an NGF antagonist in conjunction with an NSAID in accordance with the invention.

As used therein, "delaying" the development of pain means to defer, hinder, slow, retard, stabilize, and/or postpone progression of pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of pain means initial manifestations and/or ensuing progression of the disorder. Development of pain can be detectable and assessed using standard clinical techniques as well known in the art. However, development also refers to progression that may be undetectable. For purpose of this invention, development or progression refers to the biological course of the symptoms.

"Development" includes occurrence, recurrence, and onset. As used herein "onset" or "occurrence" of pain includes initial onset and/or recurrence.

An "effective amount" is an amount sufficient to effect beneficial or desired clinical results including alleviation or reduction in the pain sensation. For purposes of this invention, an effective amount of an NGF antagonist (such as an anti-NGF antibody) and an NSAID includes an amount sufficient to treat, ameliorate, reduce the intensity of or prevent pain (including nociception and the sensation of pain) of any sort, including acute, chronic, inflammatory, neuropathic, or post-surgical pain. In some embodiments, an effective amount of an NSAID and an NGF antagonist is a quantity of the NGF antagonist and the NSAID capable of modulating the sensitivity threshold to external stimuli to a level comparable to that observed in healthy subjects. In other embodiments, this level may not be comparable to that observed in healthy subjects, but is reduced compared to not receiving the combination therapy. An effective amount of an NGF antagonist also encompasses an amount of an NGF antagonist sufficient to enhance NSAID treatment (therapeutic effect) of pain, as described herein, or to reduce the dose of NSAID necessary for treatment or prevention of pain, as described herein. As is understood in the art, an effective amount of NGF antagonist in conjunction with NSAID may vary, depending on, inter alia, type of pain (and patient history as well as other factors such as the type (and/or dosage) or NGF antagonist and/or NSAID used.). An effective amount, in the context of this invention, may also be amounts of an NGF antagonist and an NSAID antagonist such that synergy is achieved. An effective amount of an antagonist in the context of this invention generally means an amount sufficient to result in enhancement of a therapeutic effect of an NSAID for pain (which can, in turn, mean that dosage is reduced and/or some other beneficial effect is observed) and/or result in a beneficial effect as compared to NSAID treatment alone. An "effective amount" of an NGF antagonist can also result in a synergistic effect as compared to administering NGF antagonist or NSAID alone.

An "individual" is a vertebrate, preferably a mammal, more preferably a human. Mammals include, but are not limited to, farm animals, sport animals, pets, primates, horses, cows, dogs, cats, mice and rats.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam.

Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

In some embodiments, aspirin and/or acetominophen are taken in conjunction with NGF antagonist (such as anti-NGF antibody). Aspirin is another type of non-steroidal anti-inflammatory compound.

As used herein, administration "in conjunction" includes simultaneous administration and/or administration at different times. Administration in conjunction also encompasses administration as a co-formulation (i.e., the NGF antagonist and NSAID are present in the same composition) or administration as separate compositions. As used herein, administration in conjunction is meant to encompass any circumstance wherein an NSAID and NGF antagonist are administered to an individual, which can occur simultaneously and/or separately. As further discussed herein, it is understood that the NGF antagonist and NSAID can be administered at different dosing frequencies or intervals. For example, an anti-NGF antibody can be administered weekly, while an NSAID can be administered more frequently. It is understood that the NGF antagonist and the NSAID can be administered using the same route of administration or different routes of administration.

"Post-surgical pain" (interchangeably termed "post-incisional" or "post-traumatic pain") refers to pain arising or resulting from an external trauma such as a cut, puncture, incision, tear, or wound into tissue of an individual (including that that arises from all surgical procedures, whether invasive or non-invasive). As used herein, post-surgical pain does not include pain that occurs (arises or originates) without an external physical trauma. In some embodiments, post-surgical pain is internal or external (including peripheral) pain, and the wound, cut, trauma, tear or incision may occur accidentally (as with a traumatic wound) or deliberately (as with a surgical incision). As used herein, "pain" includes nociception and the sensation of pain, and pain can be assessed objectively and subjectively, using pain scores and other methods well-known in the art. Post-surgical pain, as used herein, includes allodynia (i.e., increased response (i.e., a noxious perception) to a normally non-noxious stimulus) and hyperalgesia (i.e., increased response to a normally noxious or unpleasant stimulus), which can in turn, be thermal or mechanical (tactile) in nature. In some embodiments, the pain is characterized by thermal sensitivity, mechanical sensitivity and/or resting pain. In some embodiments, the post-surgical pain comprises mechanically-induced pain or resting pain. In other embodiments, the post-surgical pain comprises resting pain.

NSAID treatment of pain is "enhanced" when an aspect of NSAID treatment is improved (as compared to administering NSAID without administering an NGF antagonist). For example, efficacy of NSAID treatment of pain may be increased in the presence of NGF antagonist relative to efficacy of a NSAID in the absence of NGF antagonist. As another example, treatment or prevention of pain with an NSAID may be "enhanced" by the use of an NGF antagonist in conjunction with the NSAID when that use permits better pain relief (for example, when a dose of NSAID is used that does not permit effective treatment or prevention of pain).

Methods of the Invention

With respect to all methods described herein, reference to NGF antagonists and NSAIDs also include compositions comprising one or more of these agents. The present invention is useful for treating pain in individuals including all mammals, both human and non-human.

In one aspect, the invention provides methods of treating pain in an individual comprising administering an effective amount of an NGF antagonist (such as an anti-NGF antibody) in conjunction with an effective amount of an NSAID. In some embodiments, enough NGF antagonist will be administered so as to allow reduction of the normal dose of NSAID required to effect the same degree of pain amelioration by at least about 5%, at least about 10%, at least about 20%, at least about 30%, at least about 50%, at least about 60%, at least about 70%, at least about 80%, or at least about 90%, or more.

In another aspect, the invention provides methods of enhancing NSAID treatment of pain in an individual comprising administering an effective amount of an NGF antagonist in conjunction with an effective amount of an NSAID.

In some embodiments, pain comprises any one or more of the following: acute and/or chronic pain, any pain with an inflammatory component, post-operative pain (including dental pain), migraine, headache and trigeminal neuralgia, pain associated with burn, wound or kidney stone, pain associated with trauma (including traumatic head injury), neuropathic pain, pain associated with sickle cell crisis, pain associated with dysmenorhea or intestinal dysfunction, and pain associated with cancer (including "break-through pain" and pain associated with terminal cancer). In other embodiments, the pain is any pain that is usually treated with an NSAID (such as ibuprofen). In other embodiments, the pain is pain associated with burn. In other embodiments, the pain is pain associated with rheumatoid arthritis. In other embodiments, the pain is pain associated with osteoarthritis.

In another aspect, the invention provides methods of preventing, ameliorating and/or preventing the development or progression of pain. Thus, in some embodiments, the NGF antagonist, such as an anti-NGF antibody, and/or NSAID are administered prior to a painful event (such as surgery). For example, the NGF antagonist can be administered 30 minutes, one hour, 5 hours, 10 hours, 15 hours, 24 hours or even more, such as 1 day, several days, or even a week, 2 weeks, 3 weeks, or more prior to the activity likely to result in, or at a risk of causing pain, such as external trauma or an operation.

Treatment or prevention of pain is assessed using methods well-known in the art. Assessment may be performed based on objective measure, such as observation of behavior such as reaction to stimuli, facial expressions and the like. Assessment may also be based on subjective measures, such as patient characterization of pain using various pain scales. See, e.g., Katz et al, Surg Clin North Am. (1999) 79 (2):231-52; Caraceni et al. J Pain Symptom Manage (2002) 23(3):239-55.

Diagnosis or assessment of rheumatoid arthritis pain is well-established in the art. Assessment may be performed based on measures known in the art, such as patient characterization of pain using various pain scales. See, e.g., Katz et al, *Surg Clin North Am.* (1999) 79 (2):231-52; Caraceni et al. *J Pain Symptom Manage* (2002) 23(3):239-55. There are also commonly used scales to measure disease state such as the American College of Rheumatology (ACR) (Felson, et al., *Arthritis and Rheumatism* (1993) 36(6):729-740), the Health Assessment Questionnaire (HAQ) (Fries, et al., (1982) *J. Rheumatol.* 9: 789-793), the Paulus Scale (Paulus, et al., *Arthritis and Rheumatism* (1990) 33: 477-484), and the Arthritis Impact Measure Scale (AIMS) (Meenam, et al., *Arthritis and Rheumatology* (1982) 25: 1048-1053).

Diagnosis or assessment of osteoarthritis pain is well-established in the art. Assessment may be performed based on measures known in the art, such as patient characterization of pain using various pain scales. See, e.g., Katz et al, *Surg Clin North Am.* (1999) 79 (2):231-52; Caraceni et al. J Pain Symptom Manage (2002) 23(3):239-55. For example, WOMAC Ambulation Pain Scale (including pain, stiffness, and physical function) and 100 mm Visual Analogue Scale (VAS) may be employed to assess pain and evaluate response to the treatment.

It is understood that when an NGF antagonist (such as an anti-NGF antibody) and an NSAID are administered in conjunction, either as a single or as separate composition(s), the nerve growth factor antagonist and the NSAID are presented in a ratio which is consistent with the manifestation of the desired effect. In some embodiments, the ratio by weight of the nerve growth factor antagonist to the NSAID may be approximately 1 to 1. In some embodiments, this ratio may be between about 0.001 to about 1 and about 1000 to about 1, between about 0.01 to about 1 and about 100 to about 1, or between about 0.1 to about 1 and about 10 to about 1. Other ratios are contemplated.

It will be appreciated that the amount of a nerve growth factor antagonist and NSAID required for use in the treatment or prevention of pain will vary not only with the particular compounds or compositions selected but also with the route of administration, the nature of the condition being treated, and the age and condition of the patient, and will ultimately be at the discretion of the attending physician.

NGF Antagonists

The methods of the invention use an NGF antagonist, which refers to any molecule that blocks, suppresses or reduces (including significantly) NGF biological activity, including downstream pathways mediated by NGF signaling, such as receptor binding and/or elicitation of a cellular response to NGF. The term "antagonist" implies no specific mechanism of biological action whatsoever, and is deemed to expressly include and encompass all possible pharmacological, physiological, and biochemical interactions with NGF and its consequences which can be achieved by a variety of different, and chemically divergent, compositions. Exemplary NGF antagonists include, but are not limited to, an anti-NGF antibody, a polypeptide (including a polypeptide comprising an NGF binding domain derived from an anti-NGF antibody, e.g., a binding domain comprising CDR regions sufficient to bind NGF), an anti-sense molecule directed to an NGF (including an anti-sense molecule directed to a nucleic acid encoding NGF), an anti-sense molecule directed to either or both of the TrkA and/or p75 receptors (including anti-sense molecules directed to a nucleic aid molecule encoding trkA or p75), an NGF inhibitory compound, an NGF structural analog, a dominant-negative mutation of a TrkA receptor that binds an NGF, a TrkA immunoadhesin, an anti-TrkA antibody, an anti-p75 antibody, and a kinase inhibitor. For purpose of the present invention, it will be explicitly understood that the term "antagonist" encompass all the previously identified terms, titles, and functional states and characteristics whereby the NGF itself, an NGF biological activity (including but not limited to its ability to mediate any aspect of pain), or the consequences of the biological activity, are substantially nullified, decreased, or neutralized in any meaningful degree. In some embodiments, an NGF antagonist (e.g., an antibody) binds (physically interacts with) NGF, binds to an NGF receptor (such as TrkA and/or p75 receptor), and/or reduces (impedes and/or blocks) downstream NGF receptor signaling. Accordingly, in some embodiments, an NGF antagonist binds (physically interacts with) NGF. In other embodiment, an NGF antagonist binds to an NGF receptor (such as trkA receptor or p75). In other embodiments, an NGF antagonist reduces (impedes and/or blocks) downstream NGF receptor signaling (e.g., inhibitors of kinase signaling). In other embodiments, an NGF antagonist inhibits (reduces) NGF synthesis and/or release. In another embodiment, the NGF antagonist is a TrkA immunoadhesin. In another embodiment, the NGF antagonist is other than an anti-NGF antibody. In some embodiments, the NGF antagonist binds NGF (such as hNGF) and does not significantly bind to related neurotrophins, such as NT-3, NT4/5, and/or BDNF. In some embodiments, the NGF antagonist binds human NGF, and does not significantly bind an NGF from another vertebrate species (in some embodiments, mammalian). In some embodiments, the NGF antagonist binds human NGF as well as one or more NGF from another vertebrate species (in some embodiments, mammalian). In some embodiments, the NGF antagonist binds NGF as well as at least one other neurotrophin. In some embodiments, the NGF antagonist binds to a mammalian species of NGF, such as horse or dog, but does not significantly bind to NGF from another mammalian species.

Anti-NGF Antibodies

In some embodiments of the invention, the NGF antagonist comprises an anti-NGF antibody. An anti-NGF antibody should exhibit any one or more of the following characteristics: (a) bind to NGF and inhibit NGF biological activity and/or downstream pathway(s) mediated by NGF signaling function; (b) treating or preventing any aspect of pain, particularly in conjunction with an NSAID; (c) block or decrease NGF receptor activation (including trkA receptor dimerization and/or autophosphorylation); (d) increase clearance of NGF; (e) enhance NSAID treatment of pain.

Anti-NGF antibodies are known in the art, see, e.g., PCT Publication Nos. WO02096458; WO 01/78698, WO 01/64247, U.S. Pat. Nos. 5,844,092, 5,877,016, and 6,153,189; Hongo et al., *Hybridoma*, 19:215-227 (2000); *Cell. Molec. Biol.* 13:559-568 (1993); GenBank Accession Nos. U39608, U39609, L17078, or L17077.

In some embodiments, the anti-NGF antibody binds specifically to NGF. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In still other embodiments, the anti-NGF antibody comprises the amino acid sequence of the heavy chain variable region shown in Table 1 (SEQ ID NO:1) and the amino acid sequence of the light chain variable region shown in Table 2 (SEQ ID NO:2). In still other embodiments, the anti-NGF antibody comprises the amino acid sequence of the heavy chain variable region shown in Table 1 (SEQ ID NO:1). In still other embodiments, the anti-NGF antibody comprises the amino acid sequence of the light chain variable region shown in Table 2 (SEQ ID NO:2). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT Application No. PCT/GB99/01441; and/or UK Patent Application No. 9809951.8. In other embodiments, the anti-NGF antibody is any antibody described in U.S. Ser. No. 10/745,775.

In some embodiments, the anti-NGF antibody is a humanized mouse anti-NGF monoclonal antibody termed antibody "E3", which comprises the human heavy chain IgG2a constant region containing the following mutations: A330P331 to S330S331 (amino acid numbering with reference to the wildtype IgG2a sequence; see Eur. J. Immunol. (1999) 29:2613-2624); the human light chain kappa constant region; and the heavy and light chain variable regions shown in Tables 1 and 2.

TABLE 1

Heavy chain variable region (SEQ ID NO: 1)
QVQLQESGPGLVKPSETLSLTCTVSGFSLIGYDLNWIRQPPGKGLEWIGI

IWGDGTTDYNSAVKSRVTISKDTSKNQFSLKLSSVTAADTAVYYCARGGY

WYATSYYFDYWGQGTLVTVS.

TABLE 2

Light chain variable region (SEQ ID NO: 2)
DIQMTQSPSSLSASVGDRVTITCRASQSISNNLNWYQQKPGKAPKLLIYY

TSRFHSGVPSRFSGSGSGTDFTFTISSLQPEDIATYYCQQEHTLPYTFGQ

GTKLEIKRT.

The following polynucleotides encoding the E3 heavy chain or the E3 light chain variable region were deposited at the ATCC on Jan. 8, 2003:

| Material | | ATCC Accession No. | Date of Deposit |
|---|---|---|---|
| Vector Eb.911.3E | E3 light chain V region | PTA-4893 | Jan. 8, 2003 |
| Vector Eb.pur.911.3E | E3 light chain V region | PTA-4894 | Jan. 8, 2003 |
| Vector Db.911.3E | E3 heavy chain V region | PTA-4895 | Jan. 8, 2003 |

Vector Eb.911.3E is a polynucleotide encoding the light chain variable region shown in Table 2; vector Eb.pur.911.3E is a polynucleotide encoding the light chain variable region shown in Table 2 and vector Db.911.3E is a polynucleotide encoding the heavy chain variable region shown in Table 1. These polynucleotides also encode constant domains.

There are at least two techniques for determining CDRs: (1) an approach based on cross-species sequence variability (i.e., Kabat et al. *Sequences of Proteins of Immunological Interest*, (5th ed., 1991, National Institutes of Health, Bethesda Md.)); and (2) an approach based on crystallographic studies of antigen-antibody complexes (Chothia et al. (1989) *Nature* 342:877; Al-lazikani et al (1997) *J. Molec. Biol.* 273:927-948)). As used herein, a CDR may refer to CDRs defined by either approach or by a combination of both approaches.

In another embodiment, the anti-NGF antibody comprises one or more CDR(s) of antibody E3 (such as one, two, three, four, five, or, in some embodiments, all six CDRs from E3). Determination of CDR regions is well within the skill of the art. CDR(s) may be Kabat, Chothia, or a combination of Kabat and Chothia.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). For purposes of this invention, the antibody reacts with NGF in a manner that inhibits NGF and/or downstream pathways mediated by the NGF signaling function. In one embodiment, the antibody is a human antibody which recognizes one or more epitopes on human NGF. In another embodiment, the antibody is a mouse or rat antibody which recognizes one or more epitopes on human NGF. In another embodiment, the antibody recognizes one or more epitopes on an NGF selected from the group consisting of: primate, rodent, canine, feline, equine, and bovine. In another embodiment, the antibody comprises a modified constant region, such as a constant region that is immunologically inert (i.e., does not trigger complement mediated lysis), or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Publication No. PCT/GB99/01441; and/or UK Patent Application No. 9809951.8.

The binding affinity of an anti-NGF antibody to NGF (such as hNGF) can be about 0.01 to about 1 nM, about 0.05 to about 0.25 nM, about 0.10 to about 0.80 nM, about 0.15 to about 0.75 nM and about 0.18 to about 0.72 nM. In some embodiments, the binding affinity is about 1 pM, about 2 pM, about 5 pM, about 10 pM, about 15 pM, about 20 pM, about 40 pM, or greater than about 40 pM. In one embodiment, the binding affinity is between about 2 pM and 22 pM. In other embodiments, the binding affinity is less than about 100 nM, about 50 nM, about 10 nM, about 1 nM, about 500 pM, about 100 pM, about 50 pM, about 10 pM. In some embodiments, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM or less than about 0.07 nM. In other embodiments, the binding affinity is any of about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM. In some embodiments, the binding affinity is any of about 100 nM, about 50 nM, about 10 nM, about 1 nM, about 500 pM, about 100 pM, or about 50 pM, or less than about 50 pM. In still other embodiments, the binding affinity is about 2 pM, about 5 pM, about 10 pM, about 15 pM, about 20 pM, about 40 pM, or greater than about 40 pM.

One way of determining binding affinity of antibodies to NGF is by measuring affinity of monofunctional Fab fragments of the antibody. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiimide hydrochloride (EDC) and N-hydroxysuccinimide (NHS) according to the supplier's instructions. Human NGF can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. The chip can be blocked with ethanolamine. Regeneration studies have shown that a mixture of Pierce elution buffer (Product No. 21004, Pierce Biotechnology, Rockford Ill.) and 4 M NaCl (2:1) effectively removes the bound Fab while keeping the activity of hNGF on the chip for over 200 injections. HBS-EP buffer (0.01M HEPES, pH 7.4, 0.15 NaCl, 3 mM EDTA, 0.005% Surfactant P20) is used as running buffer for the BIAcore assays. Serial dilutions (0.1-10× estimated $K_D$) of purified Fab samples are injected for 1 min at 100 µL/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6:99-110) using the BIAevaluation program. Equilibrium dissociation constant ($K_D$) values can be calculated as $k_{off}/k_{on}$. This protocol is suitable for use in determining binding affinity of an antibody to NGF of any species, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

In some embodiments, the antibody binds human NGF, and does not significantly bind an NGF from another vertebrate species (in some embodiments, mammalian). In some embodiments, the antibody binds human NGF as well as one or more NGF from another vertebrate species (in some embodiments, mammalian, such as rodent). In still other embodiments, the antibody binds NGF and does not significantly cross-react with other neurotrophins (such as the related neurotrophins, NT3, NT4/5, and/or BDNF). In some embodiments, the antibody binds NGF as well as at least one other neurotrophin. In some embodiments, the antibody binds to a mammalian species of NGF, such as horse or dog, but does not significantly bind to NGF from another mammalian species.

The epitope(s) can be continuous or discontinuous. In one embodiment, the antibody binds essentially the same hNGF epitope as an antibody selected from the group consisting of MAb 911, MAb 912, and MAb 938 as described in Hongo et al., *Hybridoma*, 19:215-227 (2000). In another embodiment, the antibody binds essentially the same hNGF epitope as MAb 911. In still another embodiment, the antibody binds essentially the same epitope as MAb 909. Hongo et al., supra. For example, the epitope may comprise one or more of: residues K32, K34 and E35 within variable region 1 (amino acids 23-35) of hNGF; residues F79 and T81 within variable region 4 (amino acids 81-88) of hNGF; residues H84 and K88 within variable region 4; residue R103 between variable region 5 (amino acids 94-98) of hNGF and the C-terminus (amino acids 111-118) of hNGF; residue E11 within pre-variable region 1 (amino acids 10-23) of hNGF; Y52 between variable region 2 (amino acids 40-49) of hNGF and variable region 3 (amino acids 59-66) of hNGF; residues L112 and S113 within the C-terminus of hNGF; residues R59 and R69 within variable region 3 of hNGF; or residues V18, V20, and G23 within pre-variable region 1 of hNGF. In addition, an epitope can comprise one or more of the variable region 1, variable region 3, variable region 4, variable region 5, the N-terminus region, and /or the C-terminus of hNGF. In still another embodiment, the antibody significantly reduces the solvent accessibility of residue R103 of hNGF. It is understood that although the epitopes described above relate to human NGF, one of ordinary skill can align the structures of human NGF with the NGF of other species and identify likely counterparts to these epitopes.

In one aspect, antibodies (e.g., human, humanized, mouse, chimeric) that can inhibit NGF may be made by using immunogens that express full length or partial sequence of NGF. In another aspect, an immunogen comprising a cell that overexpresses NGF may be used. Another example of an immunogen that can be used is NGF protein that contains full-length NGF or a portion of the NGF protein.

The anti-NGF antibodies may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-NGF monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for NGF, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human NGF, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, $SOCl_2$, or $R1N=C=NR$, where R and R1 are different alkyl groups, can yield a population of antibodies (e.g., monoclonal antibodies).

If desired, the anti-NGF antibody (monoclonal or polyclonal) of interest may be sequenced and the polynucleotide sequence encoding the anti-NGF antibody polypeptide may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to NGF and greater efficacy in inhibiting NGF. It will be apparent to one of skill in the art that one or more polynucleotide changes can be made to the anti-NGF antibody and still maintain its binding ability to NGF.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. *Nature* 349:293-299 (1991), Lobuglio et al. *Proc. Nat. Acad. Sci. USA* 86:4220-4224 (1989), Shaw et al. *J. Immunol.* 138: 4534-4538 (1987), and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988), Verhoeyen et al. *Science* 239:1534-1536 (1988), and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT/GB99/01441; UK patent application No. 9809951.8. Other methods of humanizing antibodies that may also be utilized are disclosed by Daugherty et al., *Nucl. Acids Res.* 19:2471-2476 (1991) and in U.S. Pat. Nos. 6,180,377; 6,054,297; 5,997,867; 5,866,692; 6,210671; 6,350,861; and PCT Publication No. WO 01/27160. Other methods are described in U.S. Ser. No. 10/745,775.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., *Current Opinion in Structural Biology* 3, 564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., *J. Mol. Biol.* 222:581-597 (1991), or Griffith et al., *EMBO J.* 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., *Bio/Technol.* 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., *Nucl. Acids Res.* 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT patent application WO 9306213, published Apr. 1, 1993). Unlike traditional humanization of rodent antibodies by CDR grafting, this technique provides completely human antibodies, which have no framework or CDR residues of rodent origin. It is apparent that although the above discussion pertains to humanized antibodies, the general principles discussed are applicable to customizing antibodies for use, for example, in dogs, cats, primate, equines and bovines.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J Immunol Methods* 231:147(1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for NGF.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-NGF monoclonal antibody herein. The DNA encoding an antagonist anti-NGF antibody (such as a humanized anti-human NGF antagonist antibody) can be used for delivery and expression of antagonist anti-NGF antibody by a desired cell, as described herein. DNA delivery techniques are further described herein.

Anti-NGF antibodies may be characterized using methods well known in the art. For example, one method is to identify the epitope to which it binds, termed "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-NGF antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-NGF antibody. In another example, the epitope to which the anti-NGF antibody binds can be determined in a systematic screening by using overlapping peptides derived from the NGF sequence and determining binding by the anti-NGF antibody. According to the gene fragment expression assays, the open reading frame encoding NGF is fragmented either randomly or by specific genetic constructions and the reactivity of the expressed fragments of NGF with the antibody to be tested is determined. The gene fragments may, for example, be produced by PCR and then transcribed and translated into protein in vitro, in the presence of radioactive amino acids. The binding of the antibody to the radioactively labeled NGF fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant NGF in which various fragments of the NGF polypeptide have been replaced (swapped) with sequences from a closely related, but antigenically distinct protein (such as another member of the neurotrophin protein family). By assessing binding of the antibody to the mutant NGF, the importance of the particular NGF fragment to antibody binding can be assessed.

Yet another method which can be used to characterize an anti-NGF antibody is to use competition assays with other antibodies known to bind to the same antigen, i.e., various fragments on NGF, to determine if the anti-NGF antibody binds to the same epitope as other antibodies. Competition assays are well known to those of skill in the art. Example of antibodies that can be used in the competition assays for the present invention include MAb 911, 912, 938, as described in Hongo, et al., *Hybridoma* 19:215-227 (2000).

Other NGF Antagonists

NGF antagonists other than anti-NGF antibodies may be used. In some embodiments of the invention, the NGF antagonist comprises at least one antisense molecule capable of blocking or decreasing the expression of a functional NGF, or of functional trkA and/or p75 receptor. Nucleotide sequences of NGF, trkA and p75 are known and are readily available from publicly available databases. See, e.g., Borsani et al., *Nuc. Acids Res.* 1990, 18, 4020; Accession Number NM 002506; Ullrich et al., Nature 303:821-825 (1983). It is routine to prepare antisense oligonucleotide molecules that will specifically bind NGF, trkA or p75 mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well known in the art. See, e.g., Agrawal and Zhao (1998), *Antisense & Nucleic Acid Drug Development* 8, 135-139. Exemplary antisense molecules include the NGF antisense molecules described in U.S. Publication No. 20010046959; see also World Wide Web at rna-tec.com/repair.htm.

Alternatively, NGF expression and/or release can be decreased using gene knockdown, morpholino oligonucleotides, RNAi, or ribozymes, methods that are well-known in the art. See e.g., Rossi, J. J. et al., eds., "Intracellular Ribozyme Applications: Principles and Protocols," Horizon Scientific Press (Duarte, CA, 1999); U.S. Pat. No. 6,506,559; WO 02/244321; WO 01/192513; WO 01/29058.

In other embodiments, the NGF antagonist comprises at least one NGF inhibitory compound. As used herein, "NGF inhibitory compound" refers to a compound other than an anti-NGF antibody that directly or indirectly reduces, inhibits, neutralizes, or abolishes NGF biological activity. An NGF inhibitory compound should exhibit any one or more of the following characteristics: (a) bind to NGF and inhibit NGF biological activity and/or downstream pathway(s) mediated by NGF signaling function; (b) treating or preventing any aspect of pain, particularly in conjunction with an NSAID; (c) block or decrease NGF receptor activation (including trkA receptor dimerization and/or autophosphorylation); (d) increase clearance of NGF; (e) inhibit (reduce) NGF synthesis, production or release; (f) enhance NSAID treatment of pain. Exemplary NGF inhibitory compounds include the small molecule NGF inhibitors described in U.S. Publication No. 20010046959; the compounds that inhibit NGF's binding to p75, as described in PCT Publication No. WO 00/69829; the compounds that inhibit NGF's binding to TrkA/p75, as described in PCT Publication No. WO 98/17278. Additional examples of NGF inhibitory compounds include the compounds described in PCT Publication Nos. WO 02/17914, WO 02/20479, U.S. Pat. Nos. 5,342,942, 6,127,401, and 6,359,130. Further exemplary NGF inhibitory compounds are compounds that are competitive inhibitors of NGF. See U.S. Pat. No. 6,291,247. Furthermore, one skilled in the art can prepare other small molecules NGF inhibitory compounds.

In some embodiments, an NGF inhibitory compound binds NGF. Exemplary sites of targeting (binding) include, but are not limited to, the portion of the NGF that binds to the TrkA receptor and/or p75 receptor, and those portions of the NGF that are adjacent to the receptor-binding region and which are responsible, in part, for the correct three-dimensional shape of the receptor-binding portion. In another embodiment, an NGF inhibitory compound binds an NGF receptor (such as TrkA and/or p75) and inhibits an NGF biological activity. Exemplary sites of targeting include those portions of TrkA and/or p75 that bind to NGF.

In embodiment comprising small molecule, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In some embodiments, when the NGF-antagonist is a small molecule, it will be administered at the rate of 0.1 to 300 mg/kg of the weight of the patient divided into one to three or more doses. For an adult patient of normal weight, doses ranging from 1 mg to 5 g per dose can be administered.

In other embodiments, the NGF antagonist comprises at least one NGF structural analog. "NGF structural analogs" in the present invention refer to compounds that have a similar 3-dimensional structure as part of that of NGF and which bind to an NGF receptor under physiological conditions in vitro or in vivo. In one embodiment, the NGF structural analog binds to a TrkA and/or a p75 receptor. Exemplary NGF structural analogs include, but are not limited to, the bicyclic peptides described in PCT Publication No. WO 97/15593; the bicyclic peptides described in U.S. Pat. No. 6,291,247; the cyclic compounds described in U.S. Pat. No. 6,017,878; and NGF-derived peptides described in PCT Pub. No. WO89/09225. Suitable NGF structural analogs can also be designed and synthesized through molecular modeling of NGF-receptor binding, for example by the method described in PCT Publication No. WO 98/06048. The NGF structural analogs can be monomers or dimers/oligomers in any desired combination of the same or different structures to obtain improved affinities and biological effects.

In other embodiments, the invention provides an NGF antagonist comprising at least one dominant-negative mutant of the TrkA receptor and/or p75 receptor. One skilled in the art can prepare dominant-negative mutants of, e.g., the TrkA receptor such that the receptor will bind the NGF and, thus, act as a "sink" to capture NGFs. The dominant-negative mutants, however, will not have the normal bioactivity of the receptor (such as TrkA receptor) upon binding to NGF. Exemplary dominant-negative mutants include, but are not limited to, the mutants described in the following references: Li et al., *Proc. Natl. Acad. Sci. USA* 1998, 95, 10884; Eide et al., *J. Neurosci.* 1996, 16, 3123; Liu et al., *J. Neurosci* 1997, 17, 8749; Klein et al., *Cell* 1990, 61, 647; Valenzuela et al., *Neuron* 1993, 10, 963; Tsoulfas et al., *Neuron* 1993, 10, 975; and Lamballe et al., *EMBO J.* 1993, 12, 3083, each of which is incorporated herein by reference in its entirety. The dominant negative mutants can be administered in protein form or in the form of an expression vector such that dominant-negative mutant (e.g., a mutant TrkA receptor) is expressed in vivo. The protein or expression vector can be administered using any means known in the art, such as intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. In another embodiment, the protein or expression vector is administered directly to the sympathetic or sensory trunk or ganglion. One skilled in the art is familiar with administration of expression vectors to obtain expression of an exogenous protein in vivo. See, e.g., U.S. Pat. Nos. 6,436, 908; 6,413,942; 6,376,471.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269: 542; Zenke et al., *Proc. Natl. Acad. Sci. (USA)* (1990) 87:3655; Wu et al., *J. Biol. Chem.* (1991) 266:338. Therapeutic compositions containing a polynucleotide are administered in a range of about 100 ng to about 200 mg (or more) of DNA for local administration in a gene therapy protocol. In some embodiments, concentration ranges of less than about 500 ng, about 500 ng to about 50 mg, about 1 µg to about 2 mg, about 5 µg to about 500 µg, and about 20 µg to about 100 µg or more of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. No. 5, 219,740; 4,777,127; GB Patent No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA(see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Pat. No. 0 524 968. Additional approaches are described in Philip, *Mol. Cell Biol.* (1994) 14:2411, and in Woffendin, *Proc. Natl. Acad. Sci.* (1994) 91:1581.

It is also apparent that an expression vector can be used to direct expression of any of the protein-based NGF antagonists described herein (e.g., anti-NGF antibody, TrkA immunoadhesin, etc.). For example, a polynucleotide encoding an antagonist anti-NGF antibody may also be used for delivery and expression of antagonist anti-NGF antibody in a desired cell. It is apparent that an expression vector can be used to direct expression of an antagonist anti-NGF antibody. The expression vector can be administered intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. As discussed further herein, one skilled in the art is familiar with administration of expression vectors to obtain expression of an exogenous protein in vivo. See, e.g., U.S. Pat. Nos. 6,436,908; 6,413,942; and 6,376,471. Other TrkA receptor fragments that are capable of blocking (from partial to complete blocking) NGF and/or an NGF biological activity are known in the art.

In another embodiment, the NGF antagonist comprises at least one TrkA immunoadhesin. TrkA immunoadhesins as used herein refer to soluble chimeric molecules comprising the extracellular domain of a TrkA receptor (or a portion thereof) and an immunoglobulin sequence, which retains the binding specificity (in some embodiments, substantially retains the binding specificity) of the TrkA receptor and is capable of binding to NGF. A TrkA immunoadhesin is capable of blocking (reducing and/or suppressing) a NGF biological activity, as described herein.

TrkA immunoadhesins are known in the art, and have been found to block (reduce or suppress) the binding of NGF to the TrkA receptor. See, e.g., U.S. Pat. No. 6,153,189. In one embodiment, the TrkA immunoadhesin comprises a fusion of a TrkA receptor amino acid sequence capable of binding NGF (or an amino acid sequence that substantially retains the binding specificity of the trkA receptor) and an immunoglobulin sequence (or an amino acid that substantially retains the binding specificity of the TrkA receptor). In some embodiments, the TrkA receptor is a human TrkA receptor sequence, and the fusion is with an immunoglobulin constant domain sequence. In other embodiments, the immunoglobulin constant domain sequence is an immunoglobulin heavy chain constant domain sequence. In other embodiments, the association of two TrkA receptor-immunoglobulin heavy chain fusions (e.g., via covalent linkage by disulfide bond(s)) results in a homodimeric immunoglobulin-like structure. An immunoglobulin light chain can further be associated with one or both of the TrkA receptor-immunoglobulin chimeras in the disulfide-bonded dimer to yield a homotrimeric or homotetrameric structure. Examples of suitable TrkA immunoadhesins include those described in U.S. Pat. No. 6,153,189.

In another embodiment, the NGF antagonist comprises at least one anti-TrkA antibody capable of blocking, suppressing, altering, and/or reducing NGF physical interaction with the TrkA receptor and/or downstream signaling, whereby an NGF biological activity is reduced and/or blocked. Anti-TrkA antibodies are known in the art. Exemplary anti-TrkA antibodies include those described in PCT Publication Nos. WO 97/21732, WO 00/73344, WO 02/15924, and U.S. Publication No. 20010046959. In another embodiment, the NGF antagonist comprises at least one anti-p75 antibody capable of blocking, suppressing and/or reducing NGF physical interaction with the p75 receptor and/or downstream signaling, whereby an NGF biological activity is reduced and/or blocked.

In another embodiment, the NGF antagonist comprises at least one kinase inhibitor capable of inhibiting downstream kinase signaling associated with TrkA and/or p75 receptor activity. Exemplary kinase inhibitors are 1(252a or K252b, which are known in the art and described in Knusel et al., *J. Neurochem.* 59:715-722 (1992); Knusel et al., *J. Neurochemistry* 57:955-962 (1991); Koizumi et al., *J. Neuroscience* 8:715-721 (1988); Hirata et al., Chemical Abstracts 111:728, XP00204135, see abstract and 12th Collective Chemical Substance Index, p. 34237, c. 3 (5-7), 55-60, 66-69), p. 34238, c.1 (41-44), c.2 (25-27, 32-33), p. 3423, c.3 (48-50, 52-53); U.S. Pat. No. 6,306,849.

It is expected that a number of other categories of NGF antagonists will be identified if sought for by the clinician.

Identification of NGF Antagonists

Anti-NGF antibodies and other NGF antagonists can be identified or characterized using methods known in the art, whereby reduction, amelioration, or neutralization of an NGF biological activity is detected and/or measured. For example, a kinase receptor activation (KIRA) assay described in U.S. Pat. Nos. 5,766,863 and 5,891,650, can be used to identify anti-NGF agents. This ELISA-type assay is suitable for qualitative or quantitative measurement of kinase activation by measuring the autophosphorylation of the kinase domain of a receptor protein tyrosine kinase (hereinafter "rPTK"), e.g. TrkA receptor, as well as for identification and characterization of potential antagonists of a selected rPTK, e.g., TrkA. The first stage of the assay involves phosphorylation of the kinase domain of a kinase receptor, for example, a TrkA receptor, wherein the receptor is present in the cell membrane of a eukaryotic cell. The receptor may be an endogenous receptor or nucleic acid encoding the receptor, or a receptor construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate anti-NGF antibody or other NGF antagonist, is then added together with NGF to the wells having the adherent cells, such that the tyrosine kinase receptor (e.g. TrkA receptor) is exposed to (or contacted with) NGF and the analyte. This assay enables identification antibodies (or other NGF antagonist) that inhibit activation of TrkA by its ligand NGF. Following exposure to NGF and the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In one embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

The NGF antagonists can also be identified by incubating a candidate agent with NGF and monitoring any one or more of the following characteristics: (a) binding to NGF and inhibiting NGF biological activity and/or downstream pathway(s) mediated by NGF signaling function; (b) blocking or decreasing NGF receptor activation; (c) increasing clearance of NGF; (d) inhibiting NGF receptor activation (including TrkA dimerization and/or autophosphorylation); (e) treating, ameliorating or preventing any aspect of pain, particularly in conjunction with an NSAID; (f) inhibit (reduce) NGF synthesis, production or release; (g) enhance NSAID treatment of pain. In some embodiments, an NGF antagonist is identified by incubating an candidate agent with NGF and monitoring binding and attendant reduction or neutralization of a biological activity of NGF. The binding assay may be performed with purified NGF polypeptide(s), or with cells naturally expressing, or transfected to express, NGF polypeptide(s). In one embodiment, the binding assay is a competitive binding assay, where the ability of a candidate antibody to compete with a known NGF antagonist for NGF binding is evaluated. The assay may be performed in various formats, including the ELISA format. In other embodiments, an NGF antagonist is identified by incubating a candidate agent with NGF and monitoring attendant inhibition of TrkA receptor dimerization and/or autophosphorylation.

Following initial identification, the activity of a candidate anti-NGF antagonist can be further confirmed and refined by bioassays, known to test the targeted biological activities. Alternatively, bioassays can be used to screen candidates directly. For example, NGF promotes a number of morphologically recognizable changes in responsive cells. These include, but are not limited to, promoting the differentiation of PC12 cells and enhancing the growth of neurites from these cells (Urfer et al., Biochem. 36:4775-4781 (1997); Tsoulfas et al., Neuron 10:975-990 (1993)), promoting neurite outgrowth from explants of responsive sensory and sympathetic ganglia (Levi-Montalcini, R. and Angeletti, P. Nerve growth factor. *Physiol. Rev.* 48, 534-569, 1968) and promoting the survival of NGF dependent neurons such as embryonic dorsal root ganglion, trigeminal ganglion, or sympathetic ganglion neurons (e.g., Chun & Patterson, *Dev. Biol.* 75:705-711, (1977); Buchman & Davies, *Development* 118:989-1001, (1993). Thus, the assay for inhibition of NGF biological activity entail culturing NGF responsive cells with NGF plus an analyte, such as a candidate anti-NGF antibody and a candidate NGF antagonist. After an appropriate time the cell response will be assayed (cell differentiation, neurite outgrowth or cell survival).

The ability of a candidate NGF antagonist to block or neutralize a biological activity of NGF can also be carried out by monitoring the ability of the candidate agent to inhibit NGF mediated survival in the embryonic rat dorsal root ganglia survival bioassay as described in Hongo et al., *Hybridoma* 19:215-227 (2000). A method of identifying modulators of NGF activity is described in PCT/US2004/01609.

Compositions

The compositions of the invention comprise an effective amount of an NGF antagonist (such as anti-NGF antibody) and an NSAID, as described in various embodiments herein. In some embodiments, the compositions further comprise a pharmaceutically acceptable excipient. In some embodiments, the composition is for use in any of the methods described herein (such as methods for treating post-surgical pain). Examples of such compositions, as well as how to formulate, are also described in an earlier section and below. The NGF antagonist and NSAID may be present in a single composition or present as separate compositions. Accordingly, in some embodiments, the NGF antagonist and the NSAID are present in the same composition. In other embodiments, the NGF antagonist and NSAID are present in separate compositions.

In another aspect, the invention provides a synergistic composition of an NGF antagonist and an NSAID.

In some embodiments, the invention provides pharmaceutical compositions comprising an NGF antagonist for use in the treatment of pain (such as post-surgical pain), wherein said use comprises simultaneous and/or sequential administration of an NSAID. In some embodiments, the invention provides pharmaceutical compositions comprising an NSAID for use in the treatment of pain, wherein said use comprises simultaneous and/or sequential administration of an NGF antagonist. In some embodiments, the invention provides pharmaceutical compositions comprising an NGF antagonist and an NSAID for separate, simultaneous and/or sequential use for treatment of pain. In some embodiments, the NGF antagonist is an anti-NGF antibody (such as antibody E3 as described herein). In other embodiments, the NSAID is ibuprofen. In still other embodiments, the NGF antagonist is an anti-NGF antibody and the NSAID is ibuprofen.

It is understood that the compositions can comprise more than one NGF antagonist. For example, a composition can comprise more than one member of a class of NGF antagonist (e.g., a mixture of anti-NGF antibodies that recognize different epitopes of NGF), as well as members of different classes of NGF antagonists (e.g., an anti-NGF antibody and an NGF inhibitory compound). Other exemplary compositions comprise more than one anti-NGF antibodies that recognize the same epitope(s), different species of anti-NGF antibodies that bind to different epitopes of NGF, or different NGF inhibitory compounds. In other embodiments, the composition comprises one or more NGF antagonists selected from the group consisting of an antagonist that binds (physically interacts with) NGF (e.g., an antibody), an antagonist that binds to an NGF receptor (such as the TrkA receptor or the p75 receptor), and an antagonist that reduces (impedes and/or blocks) downstream NGF receptor signaling.

The composition used in the present invention can further comprise pharmaceutically acceptable carriers, excipients, or stabilizers (*Remington: The Science and Practice of Pharmacy* 20th Ed. (2000) Lippincott Williams and Wilkins, Ed. K. E. Hoover), in the form of lyophilized formulations or aqueous solutions. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The compositions described herein may contain additional compounds known to be useful for the treatment of pain. The NGF antagonist and NSAID, and compositions thereof can also be used in conjunction with other agents that serve to enhance and/or complement the effectiveness of the agents.

In other embodiments, the invention provides compositions (described herein) for use in any of the methods described herein, whether in the context of use as a medicament and/or use for manufacture of a medicament.

Kits

The invention also provides kits for use in the instant methods. Kits of the invention include one or more containers comprising an NGF antagonist (such as an anti-NGF antibody), an NSAID, and in some embodiments, further comprise instructions for use in accordance with any of the methods described herein. In some embodiment, the kit comprises an anti-NGF antibody (such as antibody E3 described herein). In other embodiments, the kit comprises an anti-NGF antibody comprising one or more CDR(s) of antibody E3 (such as one, two, three, four, five, or, in some embodiments, all six CDRs from E3). The kit may further comprise a description of selecting an individual suitable for treatment based on identifying whether that individual has pain or whether the individual is at risk of pain. In some embodiments, the invention provides kits for use with any of the methods described herein, said kit comprising an NGF antagonist. In still other embodiments, the kit comprises an anti-NGF antibody. In still other embodiments, the kit comprises a humanized anti-NGF antibody (such as antibody E3 described herein). In still other embodiments, the instructions comprise description of administering an NGF antagonist in conjunction with NSAIDs to treat, prevent and/or ameliorate any pain (such as post-surgical pain, pain associated with burn, rheumatoid arthritis, or osteoarthritis).

In some embodiments, the kit comprises an NGF antagonist (such as an anti-NGF antibody), an NSAID, and instructions for administering the NGF antagonist and the NSAID simultaneously and/or sequentially, for the effective treatment of pain. In another embodiment, the kit comprises an NGF antagonist (such as an anti-NGF antibody), and instructions for administering the NGF antagonist (such as anti-NGF antibody) and an NSAID in conjunction with each other, for the effective treatment of pain. In other embodiments, the kit comprises an NGF antagonist (such as an anti-NGF antibody), and an NSAID (such as ibuprofen), and instruction for administering the NGF antagonist and the NSAID in conjunction with each other, for the effective treatment of pain. Accordingly, any of the methods described herein may be reflected in the instructions.

In some embodiments, the kit comprises an anti-NGF antibody. In other embodiments, the anti-NGF antibody is an antibody comprising the heavy chain variable region shown in Table 1 and the light chain variable region shown in Table 2. In still other embodiments, the anti-NGF antibody is antibody E3 as described herein.

The NGF antagonist (such as an anti-NGF antibody) and NSAID can be present in separate containers or in a single container. It is understood that the kit may comprise one distinct composition or two or more compositions wherein one composition comprises an NGF antagonist and one composition comprises an NSAID.

The kits of this invention are in suitable packaging. Suitable packaging includes, but is not limited to, vials, bottles, jars, flexible packaging (e.g., sealed Mylar or plastic bags), and the like. Kits may optionally provide additional components such as buffers and interpretive information.

The instructions relating to the use of an NGF antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, ameliorating and/or preventing pain (including post-surgical pain). Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an NGF antagonist, such as an anti-NGF antibody. The container may further comprise a second pharmaceutically active agent.

Kits may optionally provide additional components such as buffers and interpretive information. Normally, the kit comprises a container and a label or package insert(s) on or associated with the container.

In some embodiments, the invention provides articles of manufacture comprising contents of the kits described above. In some embodiments, the kits comprise an NGF antagonist (such as anti-NGF antibody) and/or NSAID with information indicating use to treat pain (in conjunction with each other).

Administration of an NGF Antagonist and NSAID, and Assessment of Treatment

The NGF antagonist and NSAID can be administered to an individual via any suitable route. For example, they can be administered together or separately, orally, intravenously, sublingually, subcutaneously, intraarterially, intramuscularly, intraspinally, rectally, intrathoracically, intraperitoneally, intraventricularly, sublingually, transdermally or by inhalation. They can be administered orally, for example, in the form of tablets, troches, capsules, elixirs, suspensions, syrups, wafers, chewing gum, lolliopops, suppositories or the like prepared by art recognized procedures. It will be apparent to a person skilled in the art that the examples described herein are not intended to be limiting but to be illustrative of the techniques available.

Accordingly, in some embodiments, the NGF antagonist, such as an anti-NGF antibody, is administered to an individual in accordance with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, NGF antagonist (such as anti-NGF antibody) can be aerosolized using a fluorocarbon formulation and a metered dose inhaler, or inhaled as a lyophilized and milled powder.

Site-specific or targeted local delivery techniques are also useful for administration. Examples of site-specific or targeted local delivery techniques include various implantable depot sources of the NGF antagonist and/or NSAID, or local delivery catheters, such as infusion catheters, an indwelling catheter, or a needle catheter, synthetic grafts, adventitial wraps, shunts and stents or other implantable devices, site specific carriers, direct injection, use of a patient controlled analgesia (PCA) technique or device, and/or direct application. See, e.g., PCT Publication No. WO 00/53211 and U.S. Pat. No. 5,981,568.

Various formulations of agents (NGF antagonists) such as anti-NGF antibodies or fragments thereof may be used for administration. In some embodiments, agent(s) such as the anti-NGF antibodies or fragments thereof may be administered neat. In some embodiments, the agents comprise an anti-NGF antibody may be in various formulations, including formulations comprising a pharmaceutically acceptable excipient. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, et al., *The Science and Practice of Pharmacy* 20th Ed. Mack Publishing (2000).

In some embodiments, these agents (the NGF antagonists) are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history. The dosing regimen (including the NGF antagonist(s) used) can vary over time.

Anti-NGF antibodies can be administered using any suitable method, including by injection (e.g., intraperitoneally, intravenously, subcutaneously, intramuscularly, etc.). Anti-NGF antibodies can also be administered via inhalation, as described herein. Generally, for administration of anti-NGF antibodies, an initial candidate dosage can be about 0.2 mg/kg or about 2 mg/kg. In some embodiments, a typical daily dosage might range from any of about 3 μg/kg to 30 μg/kg to 300 μg/kg to 3 mg/kg to 30 mg/kg to 100 mg/kg or more, depending on the factors mentioned above. For repeated administrations over several days or longer, depending on the condition, the treatment is sustained until a desired suppression of disease symptoms occurs or until sufficient therapeutic levels are achieved to reduce the pain. An exemplary dosing regimen comprises administering an initial dose of about 2 mg/kg, followed by a weekly maintenance dose of about 1 mg/kg of the anti-NGF antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. Other dosing regimens include a regimen of up to 1 time per day, 1 to 4 times per week, or less frequently. In some embodiments, the compounds are administered about once per week, about 1 to 4 times per month. Dosage of anti-NGF antibodies are described herein. The progress of this therapy is easily monitored by conventional techniques and assays.

In some embodiments, when it is not an antibody, an NGF antagonist according to the invention may be administered at the rate of 0.1 to 300 mg/kg of the weight of the patient divided into one to three doses, or as disclosed herein. In some adult patients of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

The NSAID may be administered at a dosage level up to conventional dosage levels for such analgesics. In some embodiment, the NSAID is administered at a reduced level. Suitable dosage levels will depend upon the analgesic effect of the chosen NSAID, but typically suitable levels will be about 0.001 to 25 mg/kg per day, about 0.005 to 10 mg/kg per day, or about 0.05 to 1 mg/kg per day, or less. The compound may be administered on a regimen of up to 6 times per day (or more), 1 to 4 times per day, or it may be administered less often. In some embodiments, the NSAID is administered continuously, or very frequently (as with, for example PCA).

When administered in combination, either as a single or as separate composition(s), the nerve growth factor antagonist and the NSAID are presented in a ratio which is consistent with the manifestation of the desired effect. In some embodiments, by weight of the nerve growth factor antagonist to the NSAID will be approximately 1 to 1. In some embodiments, this ratio may be between about 0.001 to about 1 and about 1000 to about 1, between about 0.01 to about 1 and 100 to about 1, or between about 0.1 to about 1 and about 10 to about 1. Other ratios are contemplated.

It will be appreciated that the amount of a nerve growth factor antagonist and NSAID required for use in the treatment or prevention of pain will vary not only with the particular compounds or compositions selected but also with the route of administration, the nature of the condition being treated, and the age and condition of the patient, the course or stage of treatment, and will ultimately be at the discretion of the attending physician. For example, the appropriate dosage of an NGF antagonist (such as an anti-NGF antibody) will depend on the NGF antagonist(s) (or compositions thereof) employed, the type and severity of the pain to be treated, whether the agent is administered for preventive or therapeutic purposes, previous therapy, the patient's clinical history and response to the agent, and the discretion of the attending physician. Typically the clinician will administer an NGF antagonist, such as an anti-NGF antibody, until a dosage is reached that achieves the desired result.

Empirical considerations, such as the half-life, generally will contribute to the determination of the dosage. For example, antibodies that are compatible with the human immune system, such as humanized antibodies or fully human antibodies may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of pain. Alternatively, sustained continuous release formulations of an NGF antagonist and/or an NSAID may be appropriate. Various formulations and devices for achieving sustained release are known in the art.

In one embodiment, dosages for an NGF antagonist may be determined empirically in individuals who have been given one or more administration(s) of an agent that inhibits NGF activities to treat pain. Individuals are given incremental dosages of an agent that inhibits NGF, e.g., anti-NGF antibody, in conjunction with NSAID. To assess efficacy of the treatment, an indicator of pain can be followed.

Administration of an NGF antagonist and the NSAID in accordance with the method in the present invention can be continuous or intermittent, depending, for example, upon the recipient's physiological condition, whether the purpose of the administration is therapeutic or prophylactic, and other factors known to skilled practitioners. The administration of an NGF antagonist may be essentially continuous over a preselected period of time or may be in a series of spaced dose, e.g., either before, during, or after developing pain; before and after; during and after; before and during; or before, during, and after developing pain. For example, administration can be before, during and/or after wound, incision, trauma, surgery, and any other event likely to give rise to pain.

In some embodiments, more than one NGF antagonist, such as an antibody, may be present. The antagonist can be the same or different from each other. At least one, at least two, at least three, at least four, at least five, or more different NGF antagonists can be present. Generally, those NGF antagonists have complementary activities that do not adversely affect each other. NGF antagonists can also be used in conjunction with other agents that serve to enhance and/or complement the effectiveness of the agents.

In some embodiments, more than one NSAID may be present. The NSAID can be the same or different from each other. At least one, at least two, at least three, at least four, at least five or more different NSAID can be present. Generally, those NSAIDs have complementary activities that do not adversely affect each other. An NSAID(s) can also be used in conjunction with other agents that serve to enhance and/or complement the effectiveness of the agent(s).

Therapeutic formulations of the NGF antagonist (such as an antibody) and NSAID used in accordance with the present invention are prepared for storage by mixing an antibody having the desired degree of purity with optional pharmaceutically acceptable carriers, excipients or stabilizers (Remington, *The Science and Practice of Pharmacy* 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride, antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrin; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the NGF antagonist (such as an antibody) are prepared by methods known in the art, such as described in Epstein, et al., *Proc. Natl. Acad. Sci. USA* 82:3688 (1985); Hwang, et al., *Proc. Natl Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington, The Science and Practice of Pharmacy* 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-Lglutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3hydroxybutyric acid.

The formulations to be used for in vivo administration must be sterile. This is readily accomplished by, for example, filtration through sterile filtration membranes. Therapeutic NGF antagonist (such as anti-NGF antibody) compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.01 mg to about 0.1 mg to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. The active ingredients may also be incorporated in highly viscous controlled release products such as sucrose acetate isobutyrate or others. These formulations may be used either for oral dosing, or injection. The injection can result in a local depot of the drug which is released locally over the course of 1 day to three months.

Compositions for administration by injection include those comprising a NGF antagonist and an NSAID, as the active ingredients, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, or between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

In some embodiments, emulsion compositions are those prepared by mixing a nerve growth factor antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. The compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered (including orally or nasally) from devices which deliver the formulation in an appropriate manner.

Treatment efficacy can be assessed by methods well-known in the art.

The following Examples are provided to illustrate but not limit the invention.

EXAMPLES

Example 1

Treatment with Anti-NGF Monoclonal Antibody in Conjunction with an NSAID for Treating Post-Surgical Pain We used a pain model that mimics post surgical pain to assess the efficacy of an anti-NGF antibody in conjunction with the NSAID, ibuprofen. For each experiment, 16 male adult Sprague Dawley rats weighing between 200 and 220 g (Harlan; Indianapolis, Ind.) were housed under normal light conditions for at least one week prior to use with food and water ad libitum. After a 2 hour period of acclimation in the test chambers the day before surgery, the rats were divided into two groups: one received antibody 15 hours before surgery, the other received vehicle (5% Dextrose/0.45% Saline USP) at this time. Anti-NGF antagonist antibody 911 (see Hongo, et al., *Hybridoma* 19:215-227 (2000)) was given at 1 mg/kg of body weight]. Ibuprofen was given at various concentrations ranging from 10, 30, 100 and 300 mg/kg (s.c.) 24 hours after surgery to all animals.

The surgery was based on the procedure described by Brennan, et al., *Pain* 64:493-501 (1996). Animals were anesthetized with 2% isoflurane and air mixture that was maintained during surgery via a nose cone. The plantar surface of the right hind paw was prepared with a povidone-iodine pad, and a 1-cm central longitudinal incision was made through skin and fascia, starting 0.5 cm from the edge of the heel and extending toward the toes. Measurements were made with a ruler with the foot held in a flexed position. The plantaris muscle was elevated using curved forceps and incised longitudinally. The muscle was incised through its full depth, between the origin and insertion. Bleeding was controlled throughout surgery by pressure applied through a gauze pad. The wound was closed with two mattress sutures (5-0 ethicon black monofilament). These sutures were knotted 5-6 times, with the first knot loosely tied. The wound site was swabbed with bacitracin solution. Animals were allowed to recover and rest in clean cages for 22 hours before behavioral testing began.

For each experiment, the animals were divided into two groups (control and antibody-treated). Anti-NGF antibody was given 15 hours before surgery. Resting pain was assessed 22 hours after surgery in both groups ("baseline" in the following graphs). At twenty four hours post surgery, all animals were then treated with ibuprofen at 10, 30, 100 or 300 mg/kg (s.c.) mg/kg. Resting pain was assessed beginning one hour after ibuprofen treatment.

Resting pain was assessed at various times after surgery using a cumulative pain score. The rats were placed on a plastic mesh (grid: 8 mm$^2$) in a clear plastic cage and allowed to acclimate for 15 minutes-20 minutes. Behavior was assessed on a scale of 0 to 2. A score of 0 was given if the animal bore weight on the incised paw, as assessed by noting if the paw was blanched or pressed against the mesh. A score of 1 was given if the paw was favored with the skin just touching the mesh, with no blanching or indentation of the skin. A score of 2 was given if the paw was held completely off the mesh. Each animal was observed for 1 minute every 5 minutes for 30 minutes. The sum of 6 scores (0-12 total) obtained during ½-hour was used to assess pain in the incised foot.

The results of these experiments are shown in Table 1 and FIG. 1.

TABLE 1

Cumulative pain score in animals, following treatment with 1 mg/kg anti-NGF antagonist antibody and 0, 10 mg/kg, 30 mg/kg, 100 mg/kg or 300 mg/kg ibuprofen, one day after surgery.

|  | Baseline | 10 mg/kg | 30 mg/kg | 100 mg/kg | 300 mg/kg |
|---|---|---|---|---|---|
| Mab911 | 5.4 (0.8) | 3 (0.87) | 3.4 (0.68) | N/D | N/D |
| Control | 8.2 (0.72) | 7.3 (0.73) | 6.1 (1.08) | 5 (0.82) | 4.4 (0.78) |
|  | p < 0.001 | p < 0.001 | p < 0.05 |  |  |

Data are shown as mean (SEM).
Data were analyzed by one way analysis of variance and then individual pairs were analyzed using Bonferroni correction for multiple comparisons using Prizm software.

As shown in Table 1, resting pain score for Mab911 (at 1 mg/kg) treated was significantly lower than control with no ibuprofen (p<0.001). Similarly, resting pain score for 1 mg/kg Mab911 and 10 mg/kg ibuprofen treatment was significantly lower than 10 mg/kg ibuprofen treatment alone (p<0.001); and resting pain score for 1 mg/kg Mab911 and 30 mg/kg ibuprofen treatment was significantly lower than 30 mg/kg ibuprofen treatment alone (p<0.05). FIG. 1 sets forth the resting pain score measured in animals with or without treatment with 1 mg/kg of anti-NGF antibody, and with or without treatment with various doses of ibuprofen. Pre-operative treatment with anti-NGF antibody and ibuprofen is more effective in reducing resting pain than ibuprofen alone or treatment with antibody alone. It is appreciated that the Mab911 (1 mg/kg) treatment in combination with 10 mg/kg of ibuprofen is at least as effective as 300 mg/kg of ibuprofen alone.

To test the effect of treatment with anti-NGF monoclonal antibody 911 in conjunction with diclofenac for treating post-surgical pain, experiments were carried out as described above except that animals were dosed with vehicle or 5 mg/kg diclofenac instead of ibuprofen. The results are shown in FIG. 2. A reduction of pain score was observed for the mean for treatment with both 911 at 1 mg/kg and diclofenac at 5 mg/kg compared to treatment with diclofenac at 5 mg/kg alone.

Although the foregoing invention has been described in some detail by way of illustration and example for purposes of clarity of understanding, the descriptions and examples should not be construed as limiting the scope of the invention.

The invention claimed is:

1. A method for treating pain in an individual comprising administering to the individual an effective amount of an anti-nerve growth factor (NGF) antibody and an NSAID, whereby the anti-NGF antibody and the NSAID in conjunction provide effective pain relief, wherein the anti-NGF antibody comprises a heavy chain variable region comprising:
  (i) a CDR1 having the sequence 5' GFSLIGYDLN 3' (SEQ ID NO:3),
  (ii) a CDR2 having the sequence 5' IIWGDGTTDYNSAVKS 3' (SEQ ID NO:4), and
  (iii) a CDR3 having the sequence 5' GGYWYATSYYFDY 3' (SEQ ID NO:5),
and
wherein the anti-NGF antibody comprises a light chain variable region comprising:
  (i) a CDR1 having the sequence 5' RASQSISNNLN 3' (SEQ ID NO:6),
  (ii) a CDR2 having the sequence 5' YTSRFHS 3' (SEQ ID NO:7), and
  (iii) a CDR3 having the sequence 5' QQEHTLPYT 3' (SEQ ID NO:8).

2. The method of claim 1, wherein the NSAID is selected from the group consisting of ibuprofen, naproxen, naprosyn, diclofenac, ketoprofen, tolmetin, sulindac, mefanamic acid, meclofenamic acid, diflunisal, flufenisal, piroxicam, sudoxicam, isoxicam, celecoxib, fofecoxib, DUP-697, flosulide, meloxicam, 6-methoxy-2-naphthylacetic acid, MK-966, nabumetone, nimesulide, NS-398, SC-5766, SC-58215 and T-614.

3. The method of claim 1, wherein the NSAID is ibuprofen.

4. The method of claim 1, wherein the anti-NGF antibody binds human NGF.

5. The method of claim 4, wherein the anti-NGF antibody binds human NGF with a binding affinity of about 10 nM or less than about 10 nM.

6. The method of claim 4, wherein the pain is post-surgical pain.

7. The method of claim 1, wherein the pain is post-surgical pain.

8. The method of claim 1, wherein the anti-NGF antibody and the NSAID in conjunction provide a greater effect in treating pain than the corresponding amount of NSAID alone.

9. The method of claim 1, wherein the individual is a human.

10. The method of claim 1, wherein the anti-NGF antibody is a monoclonal antibody.

11. The method of claim 10, wherein the monoclonal antibody is a humanized antibody, a human antibody, a chimeric antibody, a bispecific antibody or an antibody fragment, wherein the antibody fragment is Fab, Fab', (Fab')$_2$, Fv fragments, diabodies, single chain antibody molecules, multispecific antibodies, or a single-chain Fv molecule.

12. The method of claim 10, wherein the monoclonal antibody is E3.

* * * * *